(12) United States Patent
Delcanale et al.

(10) Patent No.: US 6,951,883 B2
(45) Date of Patent: Oct. 4, 2005

(54) 2H-1-BENZOPYRAN DERIVATIVES PROCESSES FOR THEIR PREPARATION AND PHARMACEUTICAL COMPOSITIONS THEREOF

(75) Inventors: Maurizio Delcanale, Parma (IT); Gabriele Amari, Parma (IT); Elisabetta Armani, Parma (IT); Maurizio Civelli, Parma (IT); Elisabetta Galbiati, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 47 days.

(21) Appl. No.: 10/466,118

(22) PCT Filed: Jan. 21, 2002

(86) PCT No.: PCT/EP02/00567

§ 371 (c)(1),
(2), (4) Date: Dec. 22, 2003

(87) PCT Pub. No.: WO02/059113

PCT Pub. Date: Aug. 1, 2002

(65) Prior Publication Data

US 2004/0106595 A1 Jun. 3, 2004

(30) Foreign Application Priority Data

Jan. 24, 2001 (EP) .............................................. 01101521
Aug. 3, 2001 (EP) .............................................. 01118682

(51) Int. Cl.$^7$ .......................................... A61K 31/335
(52) U.S. Cl. ....................... 514/456; 514/320; 546/196; 549/399; 549/406
(58) Field of Search ............................. 549/406, 399; 546/196; 514/320, 456

(56) References Cited

U.S. PATENT DOCUMENTS 3,374,245 A * 3/1968 Carney et al. .............. 549/406
3,471,520 A * 10/1969 Irmscher et al. ............ 548/413
5,280,040 A   1/1994 Labroo et al.
5,985,306 A   11/1999 Bury et al.
6,153,768 A   11/2000 Kim et al.

FOREIGN PATENT DOCUMENTS

WO   98 18774   5/1998
WO   99 65893   12/1999
WO   00 39120   7/2000

OTHER PUBLICATIONS

Merck, "3,4–Diaryl–4–chromanols and 3,4–diaryl–3–chromenes" CA 66:28657 (1967).*
Carnet et al "Unsaturated oxacycle" CA 69:35946 (1968).*
Teo et al "Synthesis of 3–(p–fluorophenyl)–4–arylchrom–3–enes as selective ligands for antiestrogen–binding sites" CA 113:40398 (1990).*
Teo et al "Synthesis of arylchromenes and arylchromans" CA 123:313681 (1995).*
Jacobsen et al Preparation of novel (+)–enantiomers of cis–3,4–chroman derivatives useful in the prevention or treatment of estrogen related diseases or syndromes: CA 129:4580 (1998).*
T.A. Grese et al.: "Structure–activity relationships of selective estrogen receptor modulators: modifications to the 2–arylbenzothiophene core of raloxifene" Journal of Medicinal Chemsitry, vol. 40, No. 2, pp. 146–167, Oct. 17, 1997.

* cited by examiner

*Primary Examiner*—Amelia A. Owens
(74) *Attorney, Agent, or Firm*—Oblon, Spivak, McClelland, Maier & Neustadt, P.C.

(57) ABSTRACT

2H-1-Benzopyran derivatives, processes for their preparation and use thereof for the preparation of pharmaceutical compositions for the prevention and treatment of postmenopausal pathologies.

27 Claims, No Drawings

2H-1-BENZOPYRAN DERIVATIVES PROCESSES FOR THEIR PREPARATION AND PHARMACEUTICAL COMPOSITIONS THEREOF

This application is a national-stage filing under 35 U.S.C. § 371 of PCT/EP 02/00567, filed Jan. 21, 2002. This application also claims priority to EPO01001521.1, filed Jan. 24, 2001 and EPO 01118682.2, filed Aug. 3, 2001.

The present invention relates to 2H-1-benzopyran derivatives, processes for their preparation and their pharmaceutical compositions.

More precisely, the invention relates to 2H-1-benzopyran derivatives of general formula:

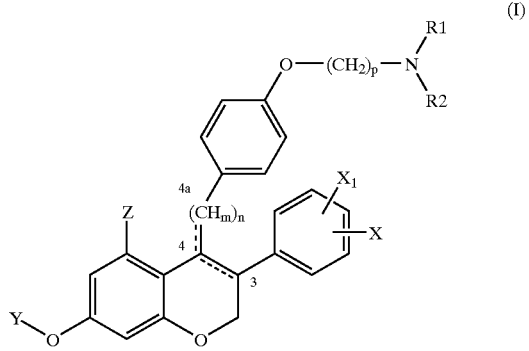

(I)

wherein $R_1$ and $R_2$ are independently H, alkyl, haloalkyl, alkenyl or haloalkenyl, or together with nitrogen atom they are bound to, can form a 4- to 8-membered heterocyclic ring X is H, alkyl, aryl, nitro, halo, O—$R_3$ wherein $R_3$ is H, alkyl, aryl, alkanoyl, aryloyl $X_1$ is H, alkyl or alkoxy and when X and $X_1$ are alkyl they can form together with the carbon atom they are bound to, a fused aromatic ring to give an α-naphthalenyl Y is H, alkyl, alkanoyl, aryloyl, alkylaminocarbonyl, alkyloxycarbonyl Z is H, O—$R_4$ wherein $R_4$ is H, alkyl, alkanoyl, aryloyl m is 1,2 n is 0,1 p is 2–6

====represents a single or double bond between the atoms in positions 3-4 or 4-4a: when n is 1 the double bond may be alternatively exocyclic or endocyclic to give respectively a 4-benzylidenechroman for m=1 or a 4-benzyl-chrom-3-ene for m=2; when n is 0 the endocyclic bond 3-4 may be a single or a double bond and when n is 0 and the endocyclic bond 3-4 is a single bond, Z is not H.

The compounds of the invention can exist in the form of salts.

The compounds bearing basic groups can exist in the form of organic or inorganic acid addition salts.

The compounds bearing acid groups can exist in the form of addition salts with alkali or alkaline-earth metal or organic amines.

When in the compounds of formula (I) the bond between 3 and 4 positions of benzopyran ring is a single bond, the two carbon atoms in 3- and 4-positions of the ring can be asymmetric, and the compounds can exist as pure enantiomer, mixture of diastereoisomers or racemates.

Alkyl is preferably a $C_1$–$C_4$ alkyl, e.g. methyl, ethyl, n-propyl, isopropyl, tert-butyl.

Haloalkyl is preferably $C_1$–$C_4$ alkyl substituted by one to five fluorine or chlorine atoms, e.g. trifluoromethyl.

Alkenyl is preferably a $C_2$–$C_4$ alkenyl, e.g. ethenyl or allyl. Haloalkenyl is preferably a $C_2$–$C_4$ alkenyl, substituted by one to three halogen atoms.

Aryl is preferably phenyl or naphthyl, optionally substituted by one to three substituents, which are the same or different, selected from halogen atoms, alkyl, alkoxy, nitro, cyano, trifluoromethyl, amino, hydroxy groups.

Alkanoyl is preferably a $C_1$–$C_4$ alkanoyl group, e.g. formyl, acetyl or propionyl group.

Aryloyl is preferably benzoyl optionally substituted by one to three substituents, which are the same or different, selected from halogen atoms, alkyl, alkoxy, nitro, cyano, trifluoromethyl, amino, hydroxy groups.

Preferred compounds of formula (I) are those wherein $R_1$ and $R_2$, taken together with the nitrogen atom, form a piperidino or a pyrrolidino ring, Y is hydrogen or an alkanoyl group, Z is hydrogen, hydroxy or alkoxy, n is zero or 1, p is 2, X and $X_1$ are hydrogen or one is hydrogen and the other is halogen or an $OR_3$ group wherein $R_3$ is as defined above, preferably in the para position.

In a preferred embodiment the invention relates to 2H-1-benzopyran derivatives of formula (IA):

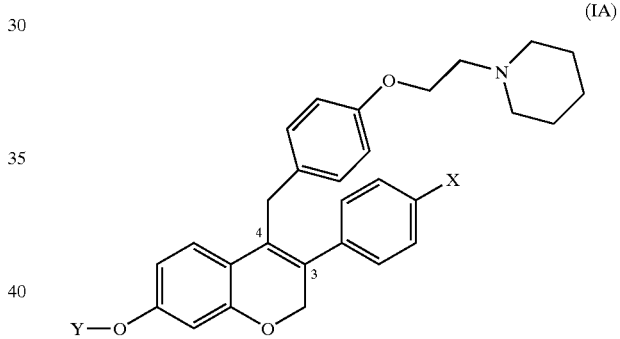

(IA)

wherein X is H, $C_1$–$C_4$ alkoxy and Y is H, $C_1$–$C_4$ alkyl, $C_1$–$C_5$ alkanoyl, aryloyl.

Aryloyl is preferably benzoyl optionally substituted by one to three substituents, which are the same or different, selected from halogen atoms, alkyl, alkoxy, nitro, cyano, trifluoromethyl, amino, hydroxy groups.

The compounds can exist in the form of organic or inorganic acid addition salts, or of addition salts with alkaline or alkaline-earth metal or with organic amines.

The compounds of formula (I) belong to the class of the Selective Estrogen Receptor Modulators (SERMs) which bind and interact with the estrogen receptor but which act in certain tissues, such as bone, as estrogen agonists and in other tissues, and in particular in the breast and uterus, as estrogen antagonists.

The SERMs retain the beneficial effects of estrogen without some of its side effects.

STATE OF THE ART

WO 94/20098 in the name of Zymogenetics discloses 3,4-diaryl-2H-1-benzopyrans for use in reducing bone loss and in particular bone loss associated with osteoporosis.

A particularly preferred compound for use within the Zymogenetics invention is the 1-enantiomer of centchroman, later developed by Novo Nordisk as levormeloxifene for the treatment of osteoporosis.

Levormeloxifene is hereinafter used as reference compound.

Substituted benzopyran and thiobenzopyran derivatives having a potential anti-estrogenic activity have been later on disclosed in WO 98/25916 and WO 99/65893, in the name of C&C Research Laboratories.

The compounds of the invention differ in their chemical structure from the benzopyrans of the prior art for:

- the presence of a double bond between the atoms in position 3-4 or 4-4a, alternatively endo- or exo-cyclic;
- the substitution on the carbon atom in 4 of the benzopyran ring with a t-aminoalkyloxybenzyl/or benzylidenyl radical;
- the presence of an hydroxy group in 5 when the substituent on the carbon in 4 is a t-aminoalkyloxyphenyl radical.

These differences in the benzopyran structure and in particular the presence of a methylene or methylidene bridge between the carbon atom in position 4 of the benzopyran ring and the carbon atom of the phenyl group has revealed of fundamental importance for the pharmacological activity of the compounds of the invention.

A non-steroidal benzothiophene derivative raloxifene, described in Jones CD et al J Med Chem 27, 1057–159, 1984, provided with tissue-specific estrogen agonist and antagonist actions has been admitted for clinical use in the US and some European countries.

The compounds of the invention favourably compare also with raloxifene.

Other synthetic compounds with this possible spectrum of activities, including triphenylethylene and dihydronaphthalene have been described as SERMs. However, the development of many of these compounds as drugs has demonstrated to be problematic due to their excessive stimulation of uterine tissue.

The novel SERMs of the invention demonstrate significant beneficial effects on bone and serum lipid levels and antagonistic effects associated with a low degree of intrinsic estrogenicity on reproductive tissue.

For their tissue-specific estrogen-agonistic and antagonistic properties the compounds of the invention can be used in therapy in particular for the prevention and treatment of a number of postmenopausal pathologies, in particular osteoporosis, coronary heart disease and estrogen dependent human cancer.

The present invention also provides a process for the preparation of a compound of formula (I)

wherein
$R_1$ and $R_2$ are independently H, alkyl, haloalkyl, alkenyl or haloalkenyl, or together with nitrogen atom they are bound to can form a 4- to 8-membered heterocyclic ring X is H, alkyl, aryl, nitro, halo, O—$R_3$ wherein $R_3$ is H, alkyl, aryl, alkanoyl, aryloyl $X_1$ is H, alkyl or alkoxy and when X and $X_1$ are alkyl they can form together with the carbon atom they are bound to, a fused aromatic ring to give an α-naphthalenyl Y is H, alkyl, alkanoyl, aryloyl Z is H, O—$R_4$ wherein $R_4$ is H, alkyl, alkanoyl, aryloyl m is 1,2 n is 0,1 p is 2–6

===represents a single or double bond between the atoms in positions 3-4 or 4-4a: when n is 1 the double bond may be alternatively exocyclic or endocyclic to give respectively a 4-benzyliden chroman for m=1 or a 4-benzyl-chrom-3-ene for m=2; when n is 0 the endocyclic bond 3-4 may be a single or a double bond and when n is 0 and the endocyclic bond 3-4 is a single bond, Z is not H.

In the schemes (1) and (2) are represented processes for the preparation of 2-(N-piperidinyl) ethoxy compounds of formula (I). These reaction schemes can also be applied to other t-aminoalkyloxy analogous of formula (I).

Compounds of formula (I) wherein Z=$OR_4$ may be obtained according to scheme (1), by reacting 1,3,5-trihydroxybenzene with a substituted phenylacetonitrile in an aprotic solvent saturated with gaseous HCl, to obtain the ketimines of formula (II) that can be hydrolyzed in boiling water to give the corresponding ketones of formula (III) that can be cyclized by means of N,N-dimethylformamide dimethylacetal and boron trifluoride diethyl etherate in dimethylformamide (DMF) to give compounds of formula (IV).

Compounds of formula (IV) can be protected in the 7-position by means, for example, of an appropriate anhydride, with or without a solvent, at temperature from 0° C. to the boiling point of the solvent or of the pure anhydride, or by means of an appropriate halide, in an aprotic solvent and in the presence of a base, to obtain an ester of formula (V) that has to be stable when submitted to the Grignard reaction.

The resulting compounds of formula (V) can be hydrogenated, in the presence of a suitable catalyst, to give compounds of formula (VI).

The addition of Grignard reagents of formula (VII), obtained from 4-(t-aminoalkyloxy)-1-bromobenzene and Mg in an aprotic solvent, to the ketones of formula (VI), at temperature from −70° C. to the boiling point of the solvent, leads to the alcohol (VIII) that can be dehydrated, for example, in an ethanolic solution of conc. HCl, to obtain compounds of formula (IX).

Compounds of formula (IX) can be alkylated or acylated by means of an alkyl or acyl halide in an appropriate solvent and in the presence of a base, or can be acylated by means of an acyl anhydride at high temperature and without a solvent, to give compounds of formula (X) where Y (different from $R_4$) is the protecting group selected from those that are stable to the Grignard reaction. Compounds of formula (IX) can be deprotected, for example with conc. HCl or conc. HBr at high temperatures, or, when Y=acyl, with $K_2CO_3$ in aqueous methanol at room temperature, to give the corresponding free phenols of formula (XI) that can be dialkylated, for example by means of an alkyl halide in an appropriate solvent and in the presence of a base, or can be diacylated, for example by means of an acyl halide in an appropriate solvent and in the presence of a base or by means of an acyl anhydride, with or without a solvent, to give compounds of formula (X) where Y is $R_4$ but different from H; compounds of formula (X) can be hydrogenated in a suitable solvent and in the presence of a catalyst, to give the corresponding compounds of formula (XII) where Y is $R_4$ or different from $R_4$ and where Y can be different from that selected as protecting group in the Grignard reaction.

Compounds of formula (IX) can also be hydrogenated to give compounds of formula (XIII).

Compounds of formula (I) wherein Z is H can be obtained following scheme (2).

Compound (XIV) was protected at the phenolic hydroxy group with an appropriate protective moiety (Y) selected from those described in the literature for the protection of phenols (see for examples T. W. Greene, P. G. Wuts "Protective groups in organic synthesis", 3rd Ed, John Wiley & Sons, Inc., 1999, pages 246–292) to obtain compound (XV). The protective group must be selected from those that are stable in the conditions of the next steps. The compound (XV) was subsequently hydrogenated selectively at the olefinic double bond, in a manner to avoid the reduction of ketone to alcohols, by means of a catalytic hydrogenation with an appropriate catalyst (containing Pd, Pt, Rh, Ru or other transition metals) in an appropriate solvent (alcohols, THF, acetone, dioxane, ethyl acetate, alcohols-water mixtures etc.) or by a chemical reduction with an hydride in an appropriate aprotic solvent, to give compound (XVI). Compound (XVI) was reacted with compound (XVII) (obtained by reaction of protected 4-hydroxybenzyl chloride with Mg in a suitable solvent like diethyl ether, THF or other ethereal solvents at temperature between r.t. and the boiling temperature of the solvent), to obtain a compound of formula (XVIII). The protective group (Y') for 4-hydroxybenzyl chloride must be selected from the same as previously described, but generally different from Y selected for compound (XV). Selective removal of this second protective group (Y') gave compound (XIX). Compounds of formula (XIX) can be alkylated with a haloalkylamine in a suitable solvent and in the presence of a base, to give compounds of formula (XX).

Compounds of formula (XX) can be dehydrated (for example with aqueous HCl in acetonitrile at room temperature) to give a mixture of compounds of formulae (XXI) and (XXII) or can be deprotected (when Y=acyl) under mild conditions, for example with $K_2CO_3$ in aqueous methanol at room temperature, to give compounds of formula (XXIII). (XXI) can be separated from the mixture by crystallization, while (XXII) can be purified by chromatographic methods.

Pure enantiomers of compounds of formula (XXI) can be obtained by chiral chromatography to give compounds of formula (XXV) and (XXVI).

Compounds of formula (XXI) and (XXII) can be hydrogenated to give compounds of formula (XXVII). Compounds of formula (XXIII) can be dehydrated, for example, with aqueous HCl in acetonitrile, to give compounds of formula (XXIV) that can be acylated or alkylated, for example, with acyl or alkyl chloride in a suitable solvent and in the presence of a base to give compounds of formula (XXII) in which Y can be different from the one selected as protecting group in the Grignard reaction.

With an appropriate choice of Y it is possible to obtain compound (XXIV) directly from compound (XX) by acidic removal of Y protective group and, simultaneously, hydrolysis of the tertiary alcohol.

Compounds of formula (XXI) where Y=acyl can be hydrolyzed for example with $K_2CO_3$ in aqueous methanol to give the corresponding phenols of formula (XXVIII) and these can be alkylated or acylated by means of an alkylating or acylating agent, to obtain compounds of formula (XXI) in which Y can be different from the one selected as protecting group in the Grignard reaction.

The preferred protecting group is pivaloyl (2,2-dimethylpropanoyl).

Scheme 1
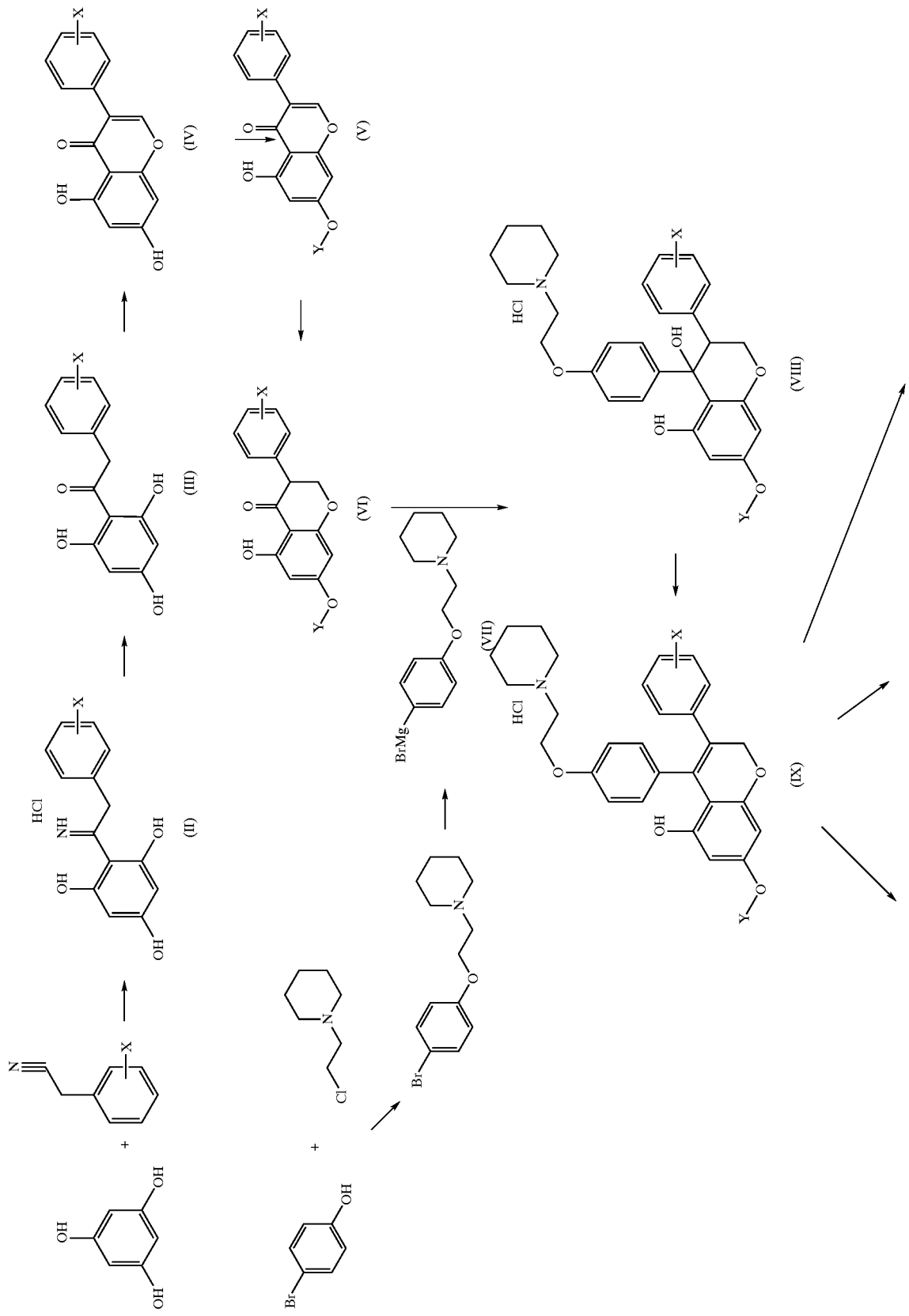

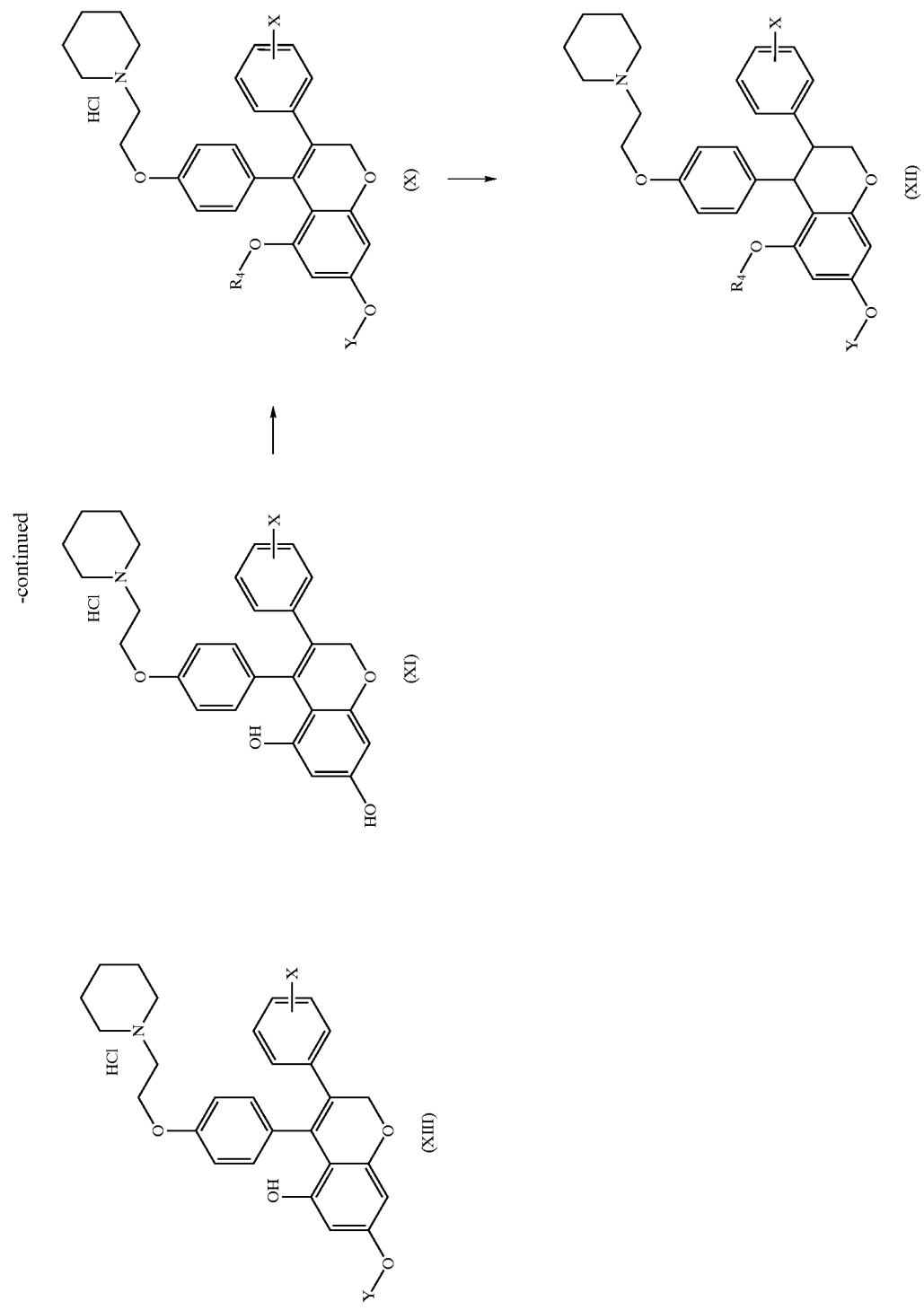

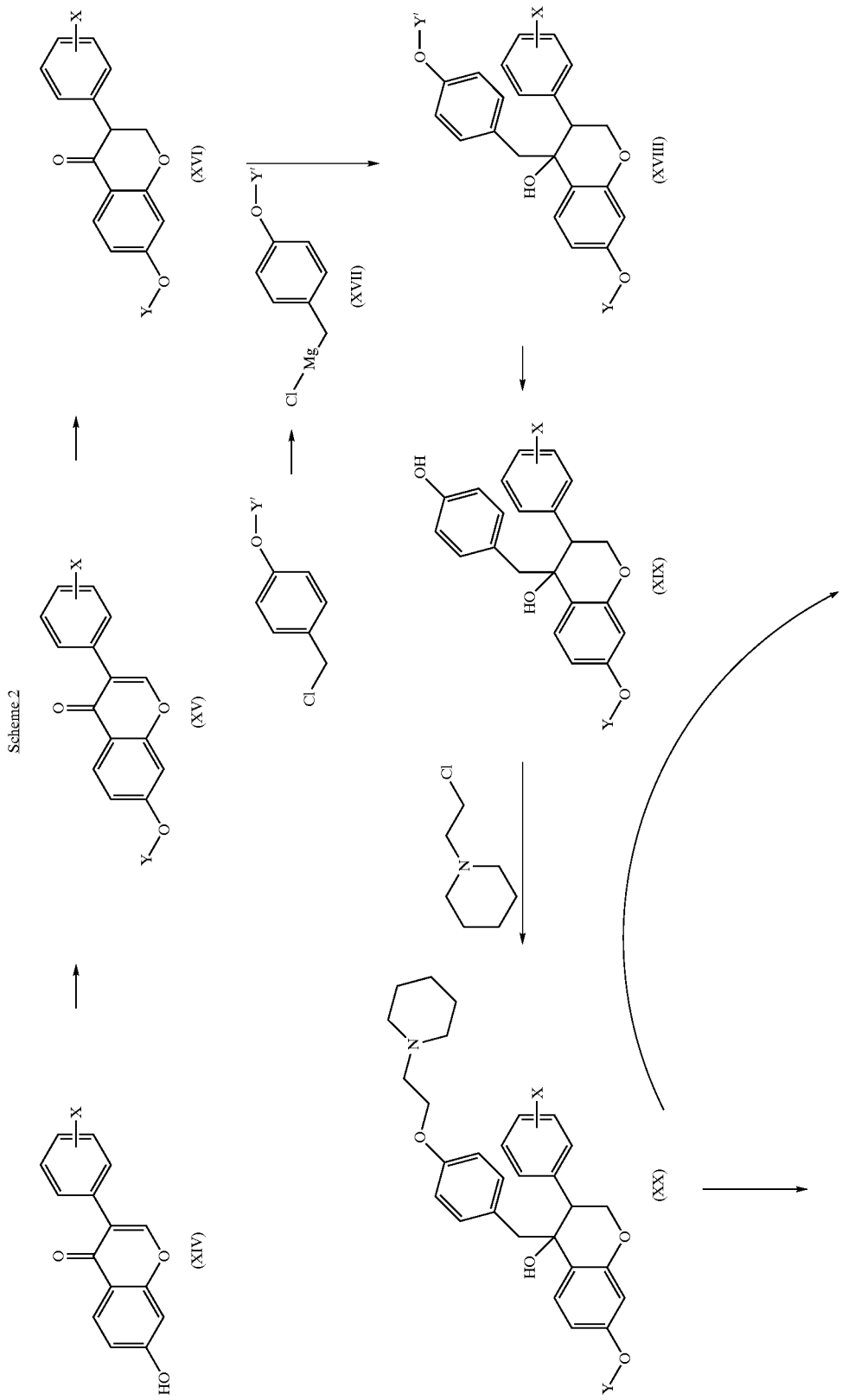

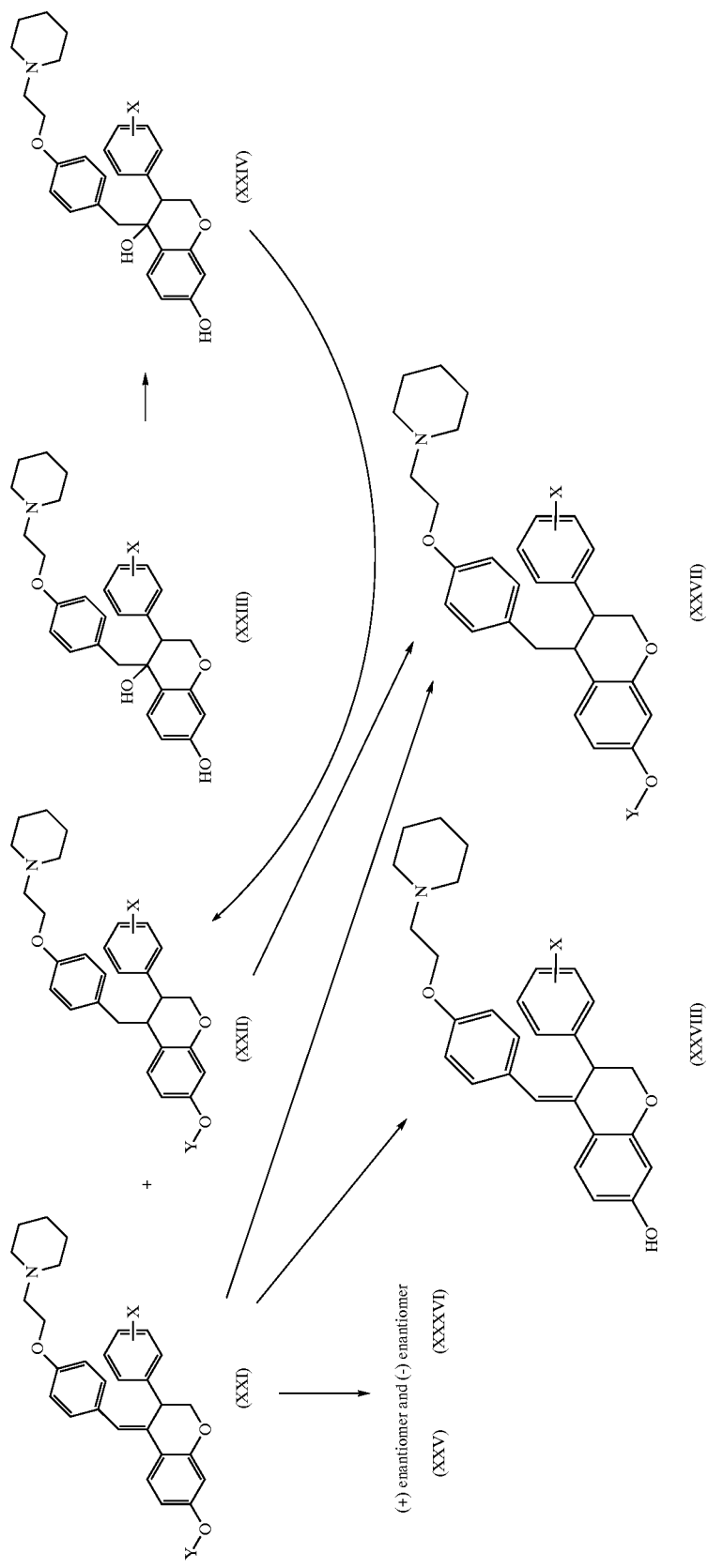

The following examples further illustrate the invention.

EXAMPLE 1

Preparation of 2,4,6-trihydroxyphenyl benzyl ketimine hydrochloride

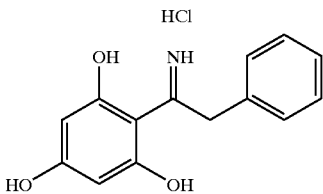

A solution of phloroglucinol (60 g) in diethyl ether (400 ml), refrigerated at 5° C., was added to a solution of phenylacetonitrile (50.1 g) and boron trifluoride diethyl etherate (4.7 ml) in HCl/ETOAc≅5M (800 ml), prepared by bubbling HCl gas in cooled ethyl acetate.

The solution was stored at 5° C. for 3 days. The crystalline yellow precipitate was filtered, washed with diethyl ether (50 ml) and used without further purification.

95 g of product were obtained (Yield=80%)
TLC: chloroform/methanol=90/10 Rf=0.7

EXAMPLE 2

Preparation of 2,4,6 trihydroxyphenyl benzylketone

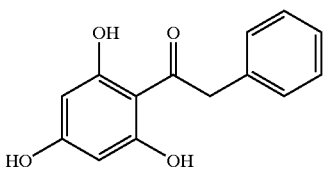

2,4,6-Trihydroxyphenyl benzylketimine hydrochloride (95 g) was suspended in water (≅2000 ml) and warmed at 90° C. under stirring for 1 hour.

After cooling, a crystalline product was obtained. The solid was filtered, washed with water (200 ml) and dried under vacuum at 60° C.

70 g of product were obtained (yield 85%)
TLC: chloroform/methanol=90/10 Rf=0.8

EXAMPLE 3

Preparation of 5,7-dihydroxyisoflavone

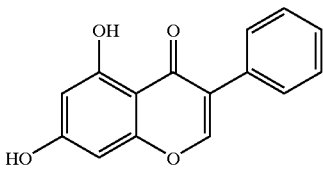

A solution of boron trifluoride diethyl etherate (228 ml) and N,N-dimethylformamide dimethylacetal (84 g) in N,N-dimethylformamide (715 ml) was added to a solution of the compound of example 2 (55 g) in N,N-dimethylformamide (1400 ml), warmed at 50° C. The mixture was heated at 95° C. for 60 minutes.

The dark orange solution was cooled at r.t., poured into cold water (10 l) and left overnight without stirring.

The pink solid was filtered, washed with water (1 l) and dried under vacuum at 70° C.

40.3 g of product were obtained (yield 70.4%)
TLC: hexane/ethyl acetate=70/30 Rf=0.55

EXAMPLE 4

Preparation of 7-pivaloyloxy-5-hydroxyisoflavone

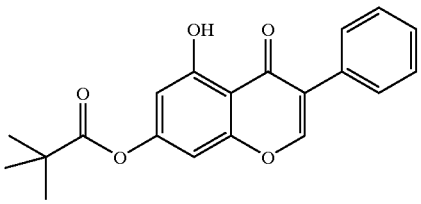

The compound of example 3 (10 g) and pivalic anhydride (50 ml) were heated at 120° C., under magnetic stirring, in a closed flask for 4 h. The red dense solution was kept at r.t. without stirring overnight.

The precipitate was filtered, washed with petroleum ether and dried u.v. at 45° C.

8.9 g of a pink solid were obtained. (yield 65%)
TLC: methylene chloride/methanol=95/5 R.f.=0.8

EXAMPLE 5

Preparation of 3-phenyl-5-hydroxy-7-pivaloyloxychroman-4-one

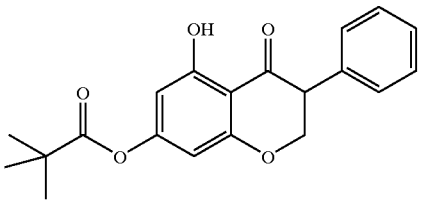

A solution of the compound of example 4 (8.7 g) in acetone (300 ml) was added with 5% Pd/C (9 g) (water content≅50%) and hydrogenated at 40 psi in a Parr apparatus for 2.5 h. The catalyst was filtered on a celite pad and the filtrate evaporated to dryness. The oily residue was dissolved in diethyl ether, dried ($Na_2SO_4$) and evaporated again. 8 g of orange oil were obtained (yield 90%).

It was used without further purification.
TLC: petroleum ether/EtOAc=95/5 R.f.=0.5

EXAMPLE 6

Preparation of 4-(2-(N-piperidinyl)ethoxy)-1-bromobenzene

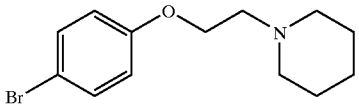

A solution of bromophenol (10 g) in dimethylformamide (160 ml) was added with $K_2CO_3$ (20.7 g) and heated at 100°

C., under stirring, for 10 min. N-(2-chloroethyl)piperidine hydrochloride (9.6 g) was added over a period of 10 min. The mixture was heated and stirred for 2 h, then cooled at r.t., poured into water (300 ml) and extracted with ethyl acetate (300 ml). The organic phase was extracted with 3% HCl (2×200 ml). After alcalinization, the aqueous phase was extracted with ethyl acetate (300 ml); evaporation of the solvent gave 13 g of product as an orange oil.

TLC: methylene chloride/methanol/acetic acid=70/20/10 R.f.=0.7

EXAMPLE 7

Preparation of 4-(2-(N-piperidinyl)ethoxy) phenylmagnesium bromide

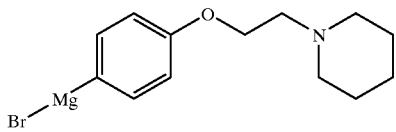

Magnesium (2.1 g) was charged into a 500 ml four necked flask, equipped with a condenser, a dropping funnel and a magnetic stirrer, under $N_2$ atmosphere.

5 ml of a solution of the compound of example 6 (11.8 g) in freshly distilled tetrahydrofuran (THF) (50 ml) was added, then the mixture was heated to reflux.

The remaining solution was dropped into the boiling reaction mixture over a period of 40 min. The mixture was allowed to reach r.t., then the turbid gray solution was used in the following step.

EXAMPLE 8

Preparation of 3-Phenyl-4-(4-(2-(N-piperidinyl) ethoxy)phenyl)-4,5-dihydroxy-7-pivaloyloxy chromane hydrochloride

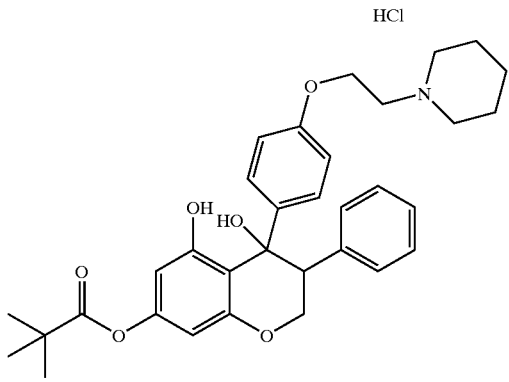

The Grignard solution obtained from the previous step was quickly added to a solution of the compound of example 5 (2.6 g ) in dry THF (20 ml), under stirring. Temperature raised to 40° C. After stirring for 1.5 h, water (10 ml) was added and the mixture evaporated to dryness u.v. The crude product was dissolved in ethyl acetate (300 ml) and the insoluble material filtered off. The organic solution was washed with HCl 0.25N (200 ml) (the hydrochloride salt of the product is more soluble in ethyl acetate than in water), and concentrated to a little volume until precipitation occurred. After ultrasonication, the solid was filtered and air dried.

1.6 g of product were obtained as a white powder. (Yield 36%).

TLC: methylene chloride/methanol=90/10 R.f.=0.3

M.P.: 220–221° C.

NMR: complies.

EXAMPLE 9

Preparation of 3-Phenyl-4-(4-(2-(N-piperidinyl) ethoxy)phenyl)-5-hydroxy-7-pivaloyl oxychrom-3-ene hydrochloride

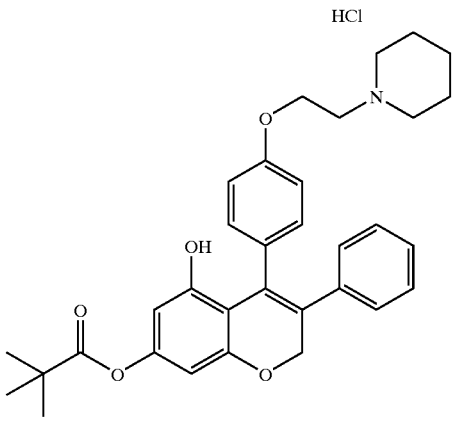

The compound of example 8 (0.71 g) was dissolved in boiling ethyl alcohol (40 ml). The solution was cooled at r.t. and HCl 37% (0.2 ml) was added. After 2 h at r.t, the solution was evaporated to complete dryness and the solid foam was crystallized from acetone. The white solid obtained was filtered, washed with acetone and dried u.v. at 35° C.

550 mg were obtained (yield 80%).

M.P.: 229–230° C.

T.L.C.: methylene chloride/methanol/triethylamine=95/5/1 R.f.=0.3

NMR: complies.

EXAMPLE 10

Preparation of 3-Phenyl-4-(4-(2-(N-piperidinyl) ethoxy)phenyl)-5-hydroxy-7-pivaloyloxychromane hydrochloride

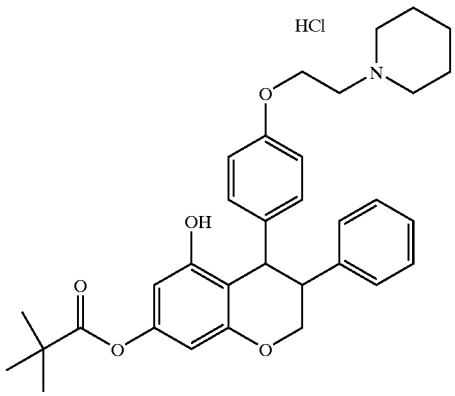

470 mg of the compound of example 9 were suspended in acetone (50 ml); $H_2O$ (2 ml) were added and the limpid solution was hydrogenated in a Parr apparatus at 40 psi with 5% Pd/C (2 g, 50% H$_2$O) for 3 h.

After filtration of the catalyst the solution was evaporated and the white solid foam obtained was dissolved in a little amount of MeOH and precipitaded by adding Et$_2$O.

230 mg of compound were obtained.

T.L.C.: methylene chloride/methanol/triethylamine=90/10/0.5

M.P.: 260–270° C. (Dec.)

NMR: complies

EXAMPLE 11

Preparation of 3-Phenyl-4-(4-(2-(N-piperidinyl)ethoxy)phenyl)-5,7-dihydroxychrom-3-ene hydrochloride

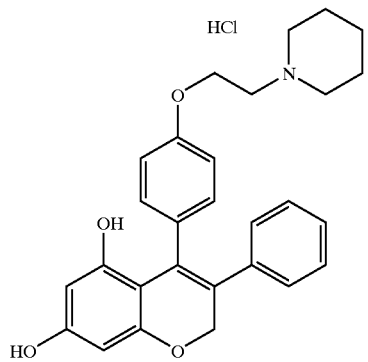

370 mg of the compound of example 9 were dissolved in hot THF (20 ml), then 130 mg of LiAlH$_4$ were added and the mixture was stirred for 30 min.

Water (170 mg) was cautiously added, the gray solid was filtered off and the solution acidified with HCl/EtOAc. The mixture was evaporated, the residue dissolved in EtOH (2 ml) and ultrasonicated.

A white solid precipitated. It was filtered, washed with Et$_2$O and dried at 50° C. u.v.

210 mg of compound were obtained.

M.P. 248–251° C. (Dec.)

T.L.C.: methylene chloride/methanol/triethylamine=95/5/1 R.f.=0.25

NMR: complies

EXAMPLE 12

Preparation of 4',7-dipivaloyloxy-5-hydroxyisoflavone

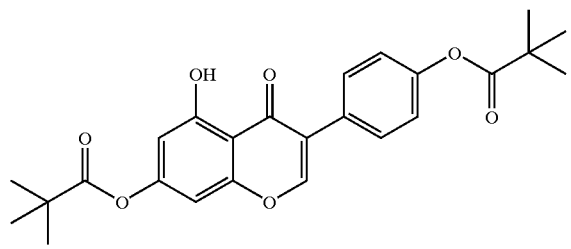

Genisteine (10 g) and pivalic anhydride (75 ml), commercially available or prepared with known methods, were heated at 110° C. for 22 h. then the brown solution was cooled and left at r.t. overnight.

A little amount of solid was formed; light petroleum ether (150 ml) was added to the mixture then the abundant solid was filtered, washed with light petroleum ether and dried u.v. at 45° C.

11.6 g of the title compound were obtained.

T.L.C.: light petroleum ether/EtOAc=85/15 R.f.=0.5.

EXAMPLE 13

Preparation of 3-(4-pivaloyloxyphenyl)-5-hydroxy-7-pivaloyloxy chroman-4-one

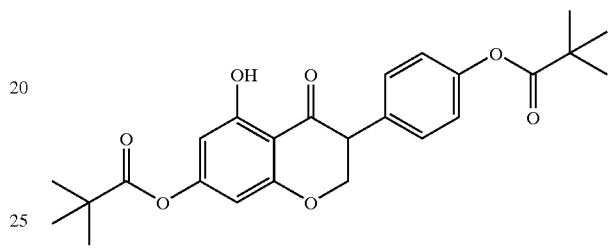

The compound of example 12 (10 g) was dissolved in acetone (750 ml) and hydrogenated at 40 psi using 5% Pd/C (10 g; 50% H$_2$O content) as catalyst.

After 3 h the catalyst was filtered off and the solution was evaporated to obtain an oil that was crystallized from light petroleum ether (150 ml).

8.7 g of the title compound were obtained.

T.L.C.: light petroleum ether/EtOAc=85/15 R.f.=0.5

EXAMPLE 14

Preparation of 3-(4-pivaloyloxyphenyl)-4-(4-(2-(N-piperidinyl)ethoxy)phenyl)-4,5-dihydroxy-7-pivaloyloxychromane hydrocloride

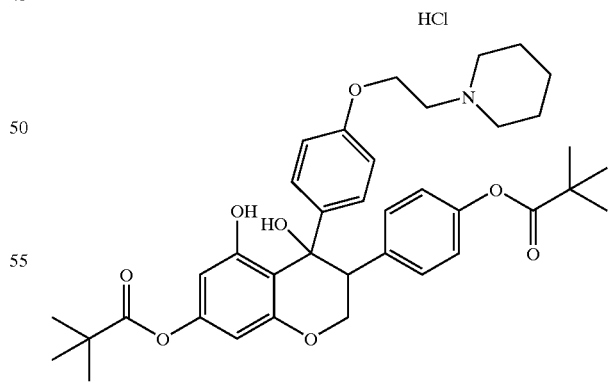

The title compound was obtained with the same procedure described in example 8 in which the compound of example 13 is used in place of the compound of example 5.

T.L.C.: chloroform/methanol/30% NH$_4$OH=95/5/0.1 R.f.=0.35

EXAMPLE 15

Preparation of 3-(4-pivaloyloxyphenyl)-4-(4-(2-(N-piperidinyl)ethoxy)phenyl)-5-hydroxy-7-pivaloyloxychrom-3-ene hydrochloride

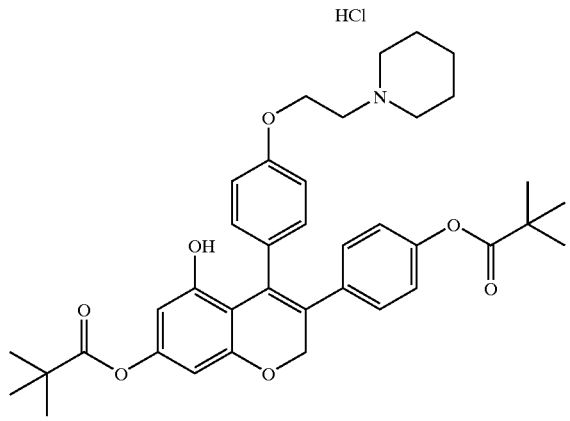

The title compound was obtained with the same procedure described in example 9 in which 3-(4-pivaloyloxyphenyl)-4-(4-(2-(N-piperidinyl)ethoxy)phenyl)-4,5-dihydroxy-7-pivaloyloxy chromane hydrochloride is used in place of the compound of example 8.

T.L.C.: chloroform/methanol/30% $NH_2OH$=95/5/0.1 R.f.=0.4

M.P.:243–245° C. (Dec.)

EXAMPLE 16

Preparation of 3-(4-pivaloyloxyphenyl)-4-(4-(2-(N-piperidinyl)ethoxy)phenyl)-5-hydroxy-7-pivaloyloxychromane hydrochloride

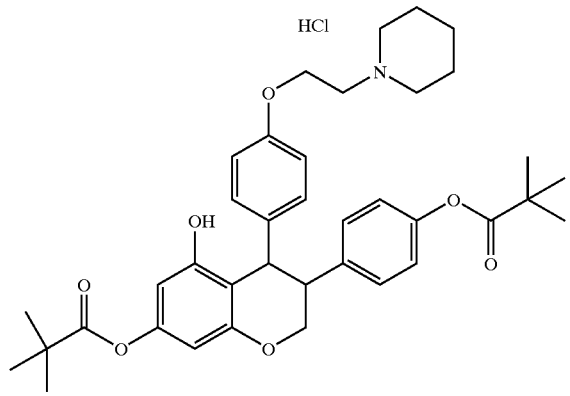

The title compound was obtained with the same procedure described in example 10 in which the compound of example 15 is used in place of the compound of example 9.

T.L.C.: chloroform/methanol/30% $NH_4OH$=95/5/0.1 R.f.=0.45

M.P.: 205–207° C. (dec.)

EXAMPLE 17

Preparation of 3-(4-pivaloyloxyphenyl)-4-(4-(2-(N-piperidinyl)ethoxy)phenyl)-5-isopropoxy-7-pivaloyloxychrom-3-ene hydrochloride

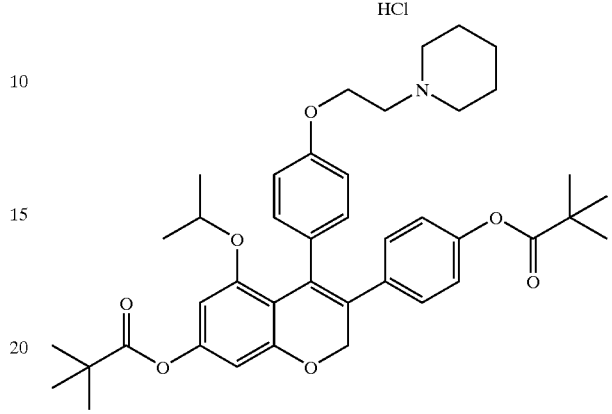

The compound of example 15 (210 mg) was dissolved in DMF (4 ml), than $K_2CO_3$ (300 mg) and 2-iodopropane (200 mg) were added and the mixture was stirred at r.t. for 2 h.

$H_2O$ (5 ml) was added, the precipitated product was filtered, washed with $H_2O$ and purified by flash chromatography over silica gel (eluent: methylene chloride/methanol= 95/5 R.f.=0.7).

The product obtained was dissolved in acetone (2 ml) and added with a little excess of HCl in EtOAc to obtain the crystalline hydrochloric salt.

7 mg of the title compound were obtained.

M.P.: 237–239° C.

NMR: complies

EXAMPLE 18

Preparation of 4'-methoxy-7-pivaloyloxy-5-hydroxyisoflavone

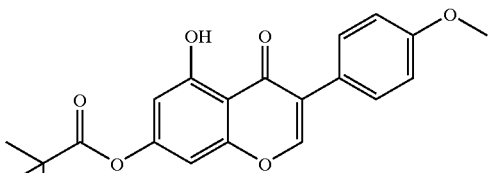

Biochanin A (20 g), commercially available or prepared with known methods, was suspended in pivalic anhydride (100 ml) and the mixture was heated at 120° C., under stirring, for 4 h.

The brown solution was left at r.t. overnight; the precipitated product was filtered, washed with light petroleum ether and dried at 70° C. u.v.

19.6 g of the title compound were obtained.

T.L.C.: methylene chloride/methanol=95/5 R.f.=0.8

EXAMPLE 19

Preparation of 3-(4-methoxyphenyl)-5-hydroxy-7-pivaloyloxychroman-4-one

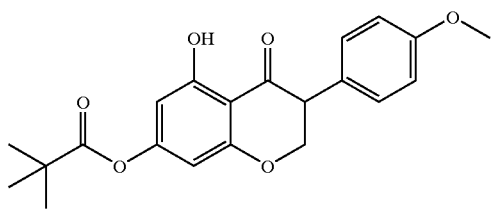

The title compound was obtained with the same procedure described in example 5 in which 4'-methoxy-7-pivaloyloxy-5-hydroxyisoflavone is used in place of the compound of example 4.

TLC: petroleum ether/EtOAc=95/5 R.f.=0.5

EXAMPLE 20

Preparation of 3-(4-methoxyphenyl)-4-(4-(2-(N-piperidinyl)ethoxy)phenyl)-4,5-dihydroxy-7-pivaloyloxychromane hydrochloride

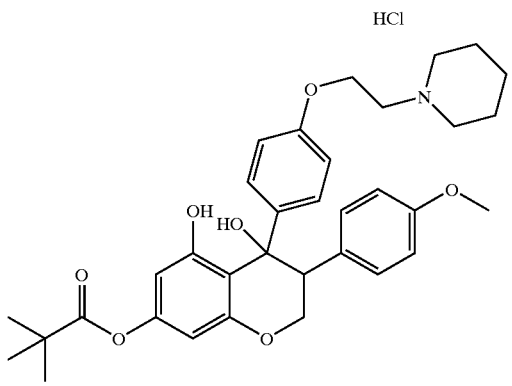

The title compound was obtained with the same procedure described in example 8 in which 3-(4-methoxyphenyl)-5-hydroxy-7-pivaloyloxychroman-4-one is used in place of the compound of example 5.

T.L.C.: chloroform/methanol/30% NH$_4$OH=95/5/0.1 R.f.=0.3

EXAMPLE 21

Preparation of 3-(4-methoxyphenyl)-4-(4-(2-(N-piperidinyl)ethoxy)phenyl)-5-hydroxy-7-pivaloyloxychrom-3-ene hydrochloride

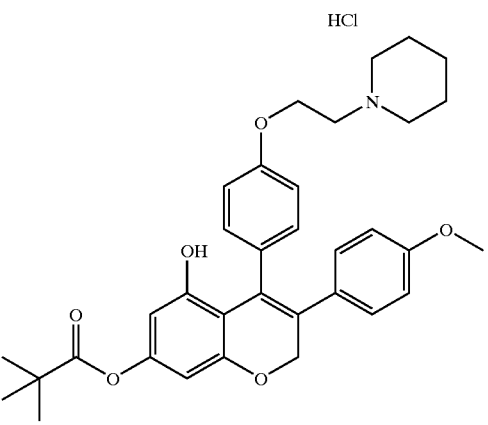

The title compound was obtained with the same procedure described in example 9 in which 3-(4-methoxyphenyl)-4-(4-(2-(N-piperidinyl)ethoxy)phenyl)-4,5-dihydroxy-7-pivaloyloxychromane hydrocloride is used in place of the compound of example 8.

T.L.C.: chloroform/methanol/30% NH$_4$OH=95/5/0.1 R.f.=0.35

M.P.: 214–216° C. (dec.)

NMR: complies

EXAMPLE 22

Preparation of 3-(4-methoxyphenyl)-4-(4-(2-(N-piperidinyl)ethoxy) phenyl)-5,7-dihydroxychrom-3-ene hydrochloride

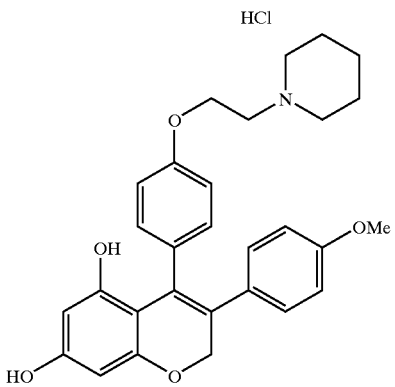

The title compound was obtained with the same procedure described in example 11 in which the compound of example 21 is used in place of the compound of example 9.

T.L.C.: chloroform/methanol/30% NH$_4$OH=95/5/1 R.f.=0.3

M.P.: 198–200° C. (dec.)

EXAMPLE 23

Preparation of 7-pivaloyloxyisoflavone

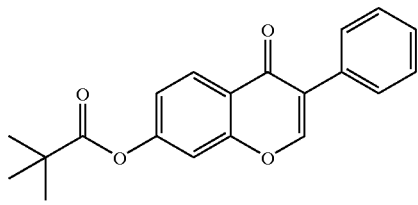

To a solution of 7 g of 7-hydroxyisoflavone in 190 ml of N,N-dimethylformamide, 2 g of sodium hydride (80% in paraffin oil) were added. The mixture was stirred for 10 minutes, then 4.2 g of pivaloyl chloride were dropped in 1 minute, under vigorous stirring. After 20 minutes at r.t. the mixture was poured into water (400 ml), the precipitate was filtered, washed with water (1000 ml) and dissolved in chloroform (800 ml). The organic solution was dried over sodium sulphate and evaporated to dryness.

7.6 g of white solid were obtained.

TLC eluent: light petroleum ether/ethyl acetate=85/15 R.f.=0.6

EXAMPLE 24

Preparation of 3-phenyl-7-pivaloyloxychroman-4-on

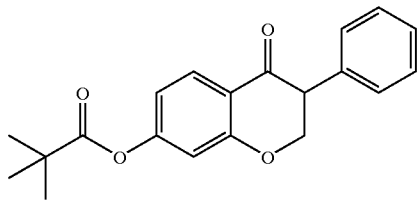

A solution of 15.7 of the compound of example 23 in 770 ml of 1,4-dioxane was added with 8 g of wet 5% palladium on carbon and hydrogenated in a Parr apparatus at 40 psi. The reaction was monitored by T.L.C. to avoid further reduction to 4-hydroxy derivatives. After 2 hours the catalyst was filtered on a celite pad and washed with 1,4-dioxane (200 ml).

The solution was evaporated to dryness and the residue oil (21.35 g) was crystallized by dissolving it in 115 ml of ethyl acetate, adding 635 ml of light petroleum ether and storing at −20° C. overnight.

8.53 g of product were obtained.

Crystallization of mother liquor in ethyl alchool gave a second crop of 1.3 g of pure product.

TLC: light petroleum ether/ethyl acetate=80/20 Rf=0.85

EXAMPLE 25

Preparation of 3-phenyl-4-(4-(2-(N-piperidinyl)ethoxy)phenyl)-4-hydroxy-7-pivaloyloxychromane hydrochloride

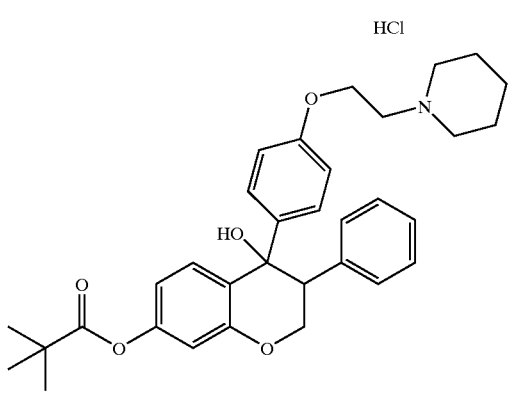

The title compound was obtained with the same procedure described in example 8 in which the compound of example 24 is used in place of example 5.

T.L.C.: methylene chloride/methanol=90/10 R.f.=0.4

EXAMPLE 26

Preparation of 3-phenyl-4-(4-(2-(N-piperidinyl)ethoxy)phenyl)-4-hydroxy-7-pivaloyloxychrom-3-ene hydrochloride

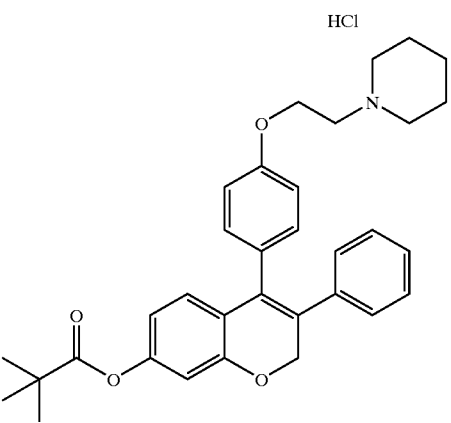

The title compound was obtained with the same procedure described in example 9 in which the compound of example 25 is used in place of the compound of example 8.

T.L.C.: methylene chloride/methanol/30% NH$_4$OH=95/5/1 R.f.=0.4

M.P.: 233–235° C. (dec.)

EXAMPLE 27

Preparation of 3-phenyl-5-hydroxy-7-methoxychroman-4-one

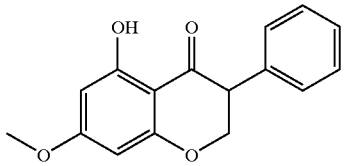

The title compound was obtained with the same procedure described in example 5 in which 5-hydroxy-7-methoxyisoflavone is used in place of the compound of example 4.

EXAMPLE 28

Preparation of 3-phenyl-4-(4-(2-(N-piperidinyl)ethoxy)phenyl)-4,5-dihydroxy-7-methoxychromane hydrochloride

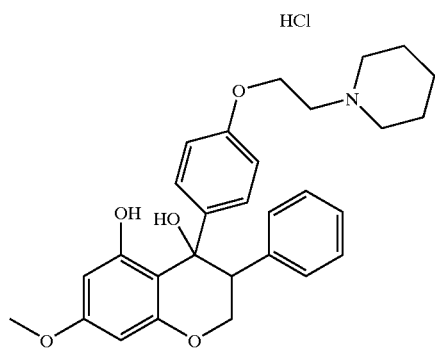

The title compound was obtained with the same procedure described in example 8 in which 3-phenyl-5-hydroxy-7-methoxychroman-4-one is used in place of the compound of example 5.

T.L.C.: methylene chloride/methanol=90/10 R.f.=0.25

EXAMPLE 29

Preparation of 3-phenyl-4-(4-(2-(N-piperidinyl)ethoxy)phenyl)-5-hydroxy-7-methoxychrom-3-ene hydrochloride

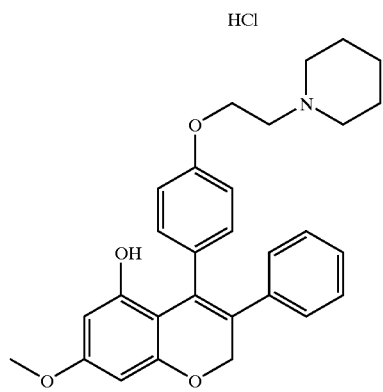

The title compound was obtained with the same procedure described in example 9 in which the compound of example 28 is used in place of the compound of example 8.

T.L.C.: methylene chloride/methanol/30% $NH_4OH$=95/5/1 R.f.=0.3

M.P.: 253–256° C. (dec.)

NMR: complies

EXAMPLE 30

Preparation of 3-Phenyl-4-(4-(2-(N-piperidinyl)ethoxy)phenyl)-5-methoxy-7-pivaloyloxychrom-3-ene hydrochloride

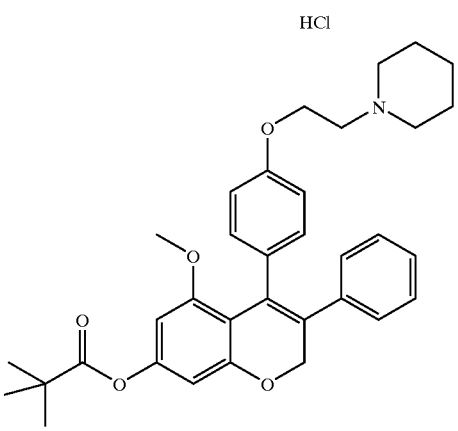

The compound of example 9 (550 mg) was dissolved in DMF (30 ml), then a solution of $K_2CO_3$ (400 mg) in $H_2O$ (3.5 ml) and a solution of $CH_3I$ (0.9 ml) in DMF (9.5 ml) were added, and the mixture was stirred for 5 h, quenched in $H_2O$ (200 ml) and extracted with EtOAc (200 ml). The organic phase was washed with brine (2×200 ml), dried over sodium sulfate and evaporated u.v. The yellow oil was purified by flash-chromatography over silica gel (eluent: $CH_2Cl_2$/MeOH/$NEt_3$=95/5/0.1 R.f.=0.4). The product obtained was transformed into its hydrochloride salt by adding HCl/EtOAc to a solution of the free base in EtOAc. 190 mg of white amorphous solid was obtained.

T.L.C.: methylene chloride/methanol/NEt3=95/5/0.1 R.f.=0.4

NMR: complies

EXAMPLE 31

Preparation of 3-(4-fluorophenyl)-4-(4-(2-(N-piperidinyl)ethoxy)phenyl)-5-hydroxy-7-pivaloyloxychrom-3-ene hydrochloride

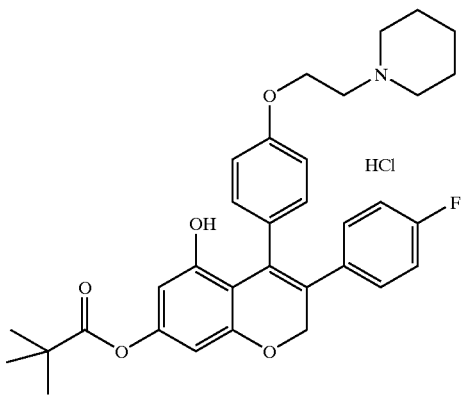

The title compound was obtained following the procedures described in examples 1 to 9 in which the starting material was 4-fluorophenylacetonitrile in place of phenylacetonitrile of example 1.

T.L.C.: methylene chloride/methanol/30% NH$_4$OH=95/5/1 R.f.=0.3

M.P.: 198–200° C. (dec.)

NMR: complies

EXAMPLE 32

Preparation of cis-3-phenyl-4-(4-benzyloxybenzyl)-4-hydroxy-7-pivaloyloxychromane

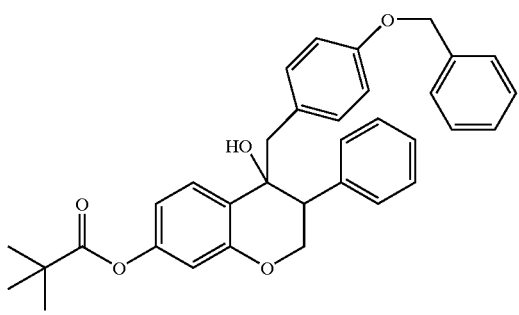

Magnesium (4.9 g) was charged, under N$_2$, in a 500 ml four necked flask, equipped with a condenser, a dropping funnel and a magnetic stirrer.

4-benzyloxybenzyl chloride (14.7 g) was dissolved in 190 ml of freshly distilled THF and charged into the dropping funnel.

10 ml of this solution were dropped over the magnesium at r.t., and the mixture strongly heated till effervescence is evident on the magnesium surface. The flask was immediately dipped into an oil bath at 75° C. and the remaining solution was added over a period of 40 min. The mixture was allowed to reach r.t., then the gray turbid solution was transferred into a 500 ml flask, equipped with a thermometer, a CaCl$_2$ valve, a magnetic stirrer and a dropping funnel, under N$_2$. The Grignard solution was immediately used in the next step or stocked in freezer. (Yield 100%, calculated weighing the unreacted magnesium).

A solution of the compound of example 24 (10 g), in freshly distilled THF(100 ml), was dropped into the above solution, refrigerated at ≅−20° C., over a period of 30 min.

The yellow-orange mixture was allowed to reach r.t., stirred for 2 hours, cooled at 0° C. and added with water (8 ml), under stirring. The solid formed was discharged, the solution was evaporated to dryness and triturated with EtOAc/light petroleum ether=15/85 (2×300 ml).

After filtration of the solid (Mg salts and other byproducts), the solution was evaporated and the oily residue was crystallized from EtOH (200 ml).

7.0 g of white solid was obtained; a second crop (1.4 g) of pure cis-3-phenyl-4-(4-benzyloxybenzyl)-4-hydroxy-7-pivaloyloxychromane was obtained by flash chromatography (EtOAc/light petroleum ether=15/85) of mother liquids.

T.L.C.: EtOAc/light petroleum ether=15/85 R.f.=0.35

EXAMPLE 33

Preparation of cis-3-phenyl-4-(4-hydroxybenzyl)-4-hydroxy-7-pivaloyloxychromane

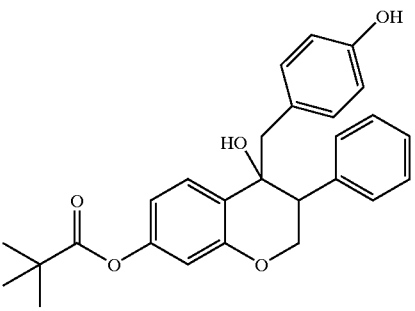

The compound of example 32 (6.9 g) was dissolved in MeOH (800 ml) and hydrogenated in a Parr apparatus with 14 g of wet 5% Pd/C at 40 psi for 45 min.

After filtration of the catalyst on a celite pad, the solution was evaporated under reduced pressure, and the oily residue was used without further purification in the following step.

T.L.C: EtOAc/light petroleum ether=30/70 R.f.=0.5

EXAMPLE 34

Preparation of cis-3-phenyl-4-(4-(2-(N-piperidinyl)ethoxy)benzyl)-4-hydroxy-7-pivaloyloxychromane

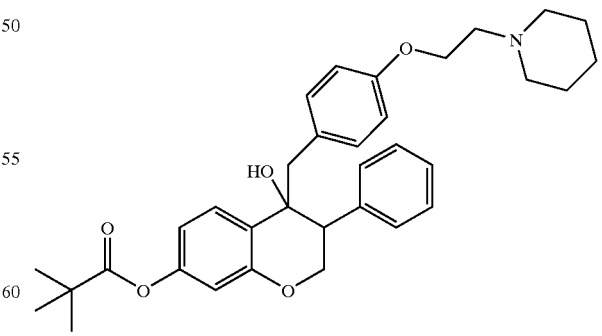

To a solution of the compound of example 33 (5.3 g) in acetone (170 ml), N-(2-chloroethyl)piperidine hydrochloride (2.48 g) and K$_2$CO$_3$ (3.38 g) were added, than the mixture was refluxed under stirring for 16 hours.

The solid was filtered off, the solution was evaporated and the oily residue was dissolved in boiling hexane (500 ml).

After filtration of the insoluble material, the hot solution was cooled at r.t. and ultrasonicated (or vigorously stirred) until crystallization occurred. After storage at −20° C., the solid was filtered and dried u.v. at 50° C.

3.2 g of a white solid were obtained.

Mother liquids can be submitted to flash chromatography ($CH_2Cl_2$/MeOH/$NEt_3$=95/5/0.1) to give additional 1.2 g of product.

T.L.C.: methylene chloride/methanol/$NEt_3$=95/5/0.1 R.f.=0.4

EXAMPLE 35

Preparation of rac-3-phenyl-4-E-(4-(2-(N-piperidinyl)ethoxy)benzyliden-7-pivaloyl oxychromane hydrochloride

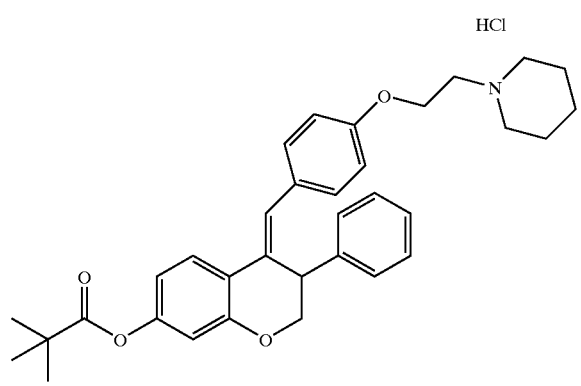

A solution of the compound of example 34 (4.2 g) in $CH_3CN$ (300 ml), refrigerated at −20° C., was added to a cold (−20° C.) solution of 37% HCl (3 ml) in $CH_3CN$ (300 ml), and left at −20° C. overnight.

The solution was allowed to reach r.t. and checked by H.P.L.C.

When the compound of example 34 was completely consumed, the solvent was evaporated under vacuum, the residue was dissolved in acetone and evaporated again, to obtain a white solid foam that was dissolved in EtOAc and crystallized by ultrasonication or by stirring.

T.L.C.: EtOAc/n-ButOH/$H_2O$/$CH_3COOH$=50/10/10/10 R.f.=0.3

M.P.:214–216° C.

NMR: complies

EXAMPLE 36

Separation of Enantiomers of the Compound of Example 35

The compound of example 35 was submitted to preparative H.P.L.C. separation.

The conditions of the preparative separation are listed below:

Column:Chorisis 10 μm, 7.8×300 mm
Eluent: Acetonitrile/0.5% acetic acid=25/75
Flow: 2 ml/min
λ: 254 nm
Charge: 25 mg dissolved in 0.5 ml of mobil phase.

The enantiomeric purity of the two enantiomers was determined by analytical chiral chromatography; conditions are listed above:

Column:Chiralcel OJ-R, 5 μm, 4.6×150 mm

Eluent: Acetonitrile/0.01M $NaH_2PO_4$+1 ml $HCLO_4$ (pH=5.6)=65/35

Flow: 0.5 ml/min

λ: 254 nm

Retention time of the (+) isomer: 5.6 min

Retention time of the (−) isomer: 6.2 min

The two isomers were collected as free base

They were converted into their hydrochloride salt by bubbling HCl gas into an ethereal solution of the free bases.

$[\alpha]_D$=+44.6 (c=1, MeOH)

$[\alpha]_D$=−44.0 (c=1, MeOH)

EXAMPLE 37

Preparation of rac-3-phenyl-4-E-(4-(2-(N-piperidinyl)ethoxy)benzyliden-7-hydroxychromane hydrochloride

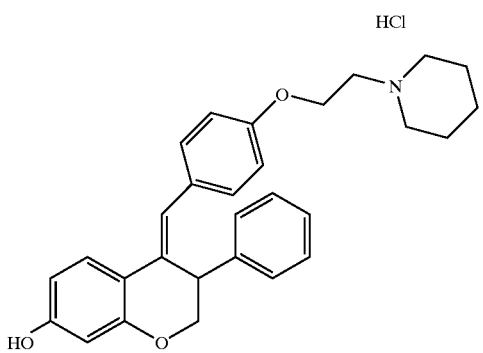

A solution of $K_2CO_3$ (440 mg) in $H_2O$ (2.5 ml) was added to a solution of the compound of example 35 (440 mg) in MeOH (50 ml) and stirred overnight. 1N HCl (6.3 ml) was added, then the solution was partially evaporated until a white emulsion was formed. After cooling to 0° C., a solid separated that was filtered, washed with water and air-dried. 320 mg of white amorphous solid was obtained.

T.L.C.: EtOAc/n-ButOH/$H_2O$/$CH_3COOH$=50/10/10/10 R.f.=0.2

NMR: complies

EXAMPLE 38

Preparation of cis-3-phenyl-4-(4-(2-(N-piperidinyl)ethoxy)benzyl)-4,7 dihydroxychromane

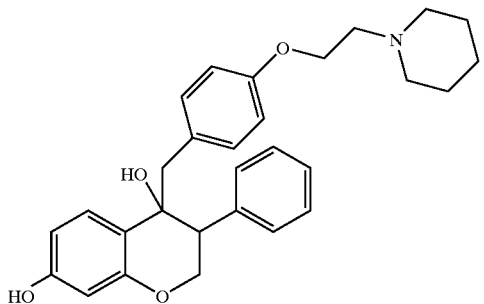

A mixture of the compound of example 34 (12.5 g), MeOH (800 ml), $K_2CO_3$ (12.5 g) and $H_2O$ (40 ml) was stirred for 4 h, the solvent was evaporated to 50 ml and $H_2O$ (500 ml) was added, under magnetical stirring. A white solid separated and was collected by filtration, washed with water and dried at 45° C. 9.2 g of the title compound were obtained.

T.L.C.: methylene chloride/methanol/30% $NH_4OH$=93/7/0.7 R.f.=0.35

M.P. 95–103° C.

NMR: complies

EXAMPLE 39

Preparation of 3-phenyl-4-(4-(2-(N-piperidinyl)ethoxy)benzyl)-7-hydroxychrom-3-ene

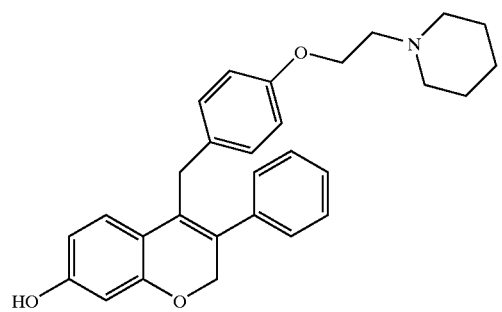

A solution of 37% HCl (3 ml) in acetonitrile (40 ml) was added to a boiling solution of the compound of example 38 (9 g) in acetonitrile (300 ml). After 20 min the solution was quickly refrigerated to 0° C., added with $K_2CO_3$ (9.0 g), stirred for 3 hours and the precipitated free base together with $K_2CO_3$ was filtered, washed with water and dried under vacuum at 40 C.

To obtain 7 g of the title compound:

M.P.: 168–170° C. (Dec.)

T.L.C.: methylene chloride/methanol/30% $NH_4OH$=93/7/0.7 R.f.=0.4

NMR: complies

EXAMPLE 40

Preparation of 3-phenyl-4-(4-(2-(N-piperidinyl)ethoxy)benzyl)-7-pivaloyloxychrom-3-ene hydrochloride

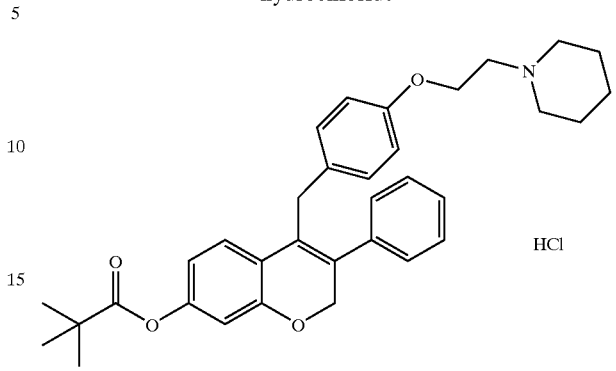

Pivaloyl chloride (0.5 g) was added to a mixture of the compound of example 39 (0.5 g) and $K_2CO_3$ (0.5 g) in acetonitrile (40 ml); the mixture was stirred for 5 h, the salts were filtered off, then HCl in EtOAc (slight excess) was added and the solution was evaporated to dryness to leave a solid foam that was triturated with ethyl ether, filtered and dried al r.t.

400 mg of the title compound were obtained as a white amorphous solid.

T.L.C.: EtOAc/n-ButOH/$H_2O$/$CH_3COOH$=50/10/10/10 R.f.=0.4

NMR: complies

EXAMPLE 41

Preparation of 3-phenyl-4-(4-(2-(N-piperidinyl)ethoxy)phenyl)-5,7-diacetyloxychrom-3-ene hydrochloride

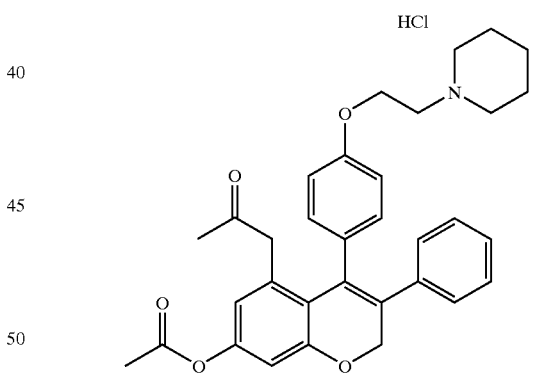

The compound of example 11 (210 mg, prepared as in example 11) was dissolved in acetic anhydride (2 g) at 130° C. and stirred for 30 min. The solution was cooled to room temperature, added with ice (2 g), diluted with water (50 ml) treated with aqueous $K_2CO_3$ and extracted with EtOAc (50 ml). The organic layer was dried over sodium sulfate, filtered, acidified with a slight excess of HCl/EtOAc and evaporated to dryness. The yellow oil resulting was crystallized from acetone/$Et_2O$ to give 100 mg of the title compound as a light-yellow powder.

T.L.C. methylene chloride/methanol/$NEt_3$=95/5/0.1 R.f.=0.55

M.P. 154–156° C. (Dec.)

NMR: complies

EXAMPLE 42

Preparation of 3-phenyl-4-(4-(2-(N-piperidinyl)ethoxy)benzyl)-7-isobutyroyloxychrom-3-ene hydrochloride

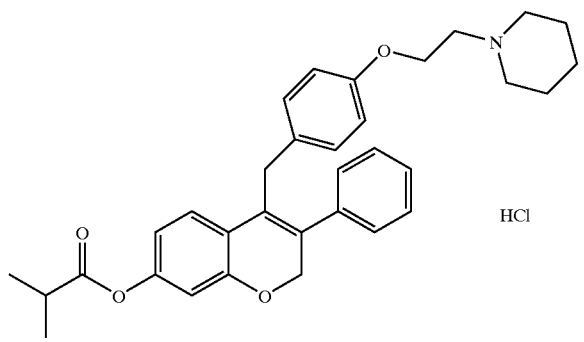

The title compound was obtained following the procedures described in example 40 in which isobutyroyl chloride is used in place of pivaloyl chloride.

T.L.C.: EtOAc/n-ButOH/$H_2O$/$CH_3$COOH=50/10/10/10 R.f.=0.4

M.P.=152–155° C.

NMR: complies

EXAMPLE 43

Preparation of 3-phenyl-4-(4-(2-(N-piperidinyl)ethoxy)benzyl)-7-hydroxychrom-3-ene methansulfonate (1:1) (soluble salt of the compound of example 39)

2.7 g of the compound of example 39 were dissolved in 120 ml of hot acetone, then a solution of 512 mg of methansulphonic acid in 30 ml of acetone was added and the solution was magnetically stirred until crystallization occurred.

After standing at −20° C. for 2 h, the solid was filtered, washed with Et2O and dried under vacuum at 40° C.

2.9 g of a white solid were obtained. M.P.=170–175° C. (Dec.)

The solubility of this salt in water at r.t. was >1 mg/ml.

EXAMPLE 44

Preparation of 3-phenyl-4-(4-(2-(N-piperidinyl)ethoxy)benzyl)-7-hydroxychrom-3-ene by isomerization of the compound of example 37

25 ml of 1% HCl conc. in $CH_3CN$ were added to a suspension of the compound of the example 37 (660 mg) in $CH_3CN/H_2O$ (150/5 ml) heated at 80° C. The reaction was monitored in HPLC (column Select B RP $C_{18}$, eluent: $CH_3$CN-MeOH=80–20 70%, buffer 30%, flow=0.8 ml/min, λ=254 nm). After 15 min of heating at 80° C. the reaction finished: 85% of the product (retention time=4.8 min) formed and 11% of the reagent remained unreacted. The reaction didn't proceed further, neither continuing the heating, nor adding a larger amount of acid.

The reaction mixture was worked up and the product was isolated as described in the example 39.

500 mg of the product were obtained (yield 75%).

EXAMPLE 45

Preparation of 2,2-dimethyl-propanoic acid 3-(4-methoxyphenyl)-4-oxo-4H-1-benzopyran-7-yl ester

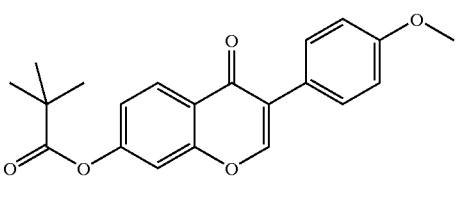

Formononetine (90 g; 335 mmol) was suspended in acetonitrile, $K_2CO_3$ was added and the mixture was stirred for about 20 minutes at r.t. Pivaloyl chloride (59.85 g; 496 mmol) was dropped into the mixture, then the reaction was stirred for further 15 minutes and quenched into water. The solid was filtered, washed with water, dissolved in $CHCl_3$; the solution was dried and evaporated to dryness to obtain the title compound, which can be crystallised from hot toluene. 102 g of a white crystalline powder were obtained.

M.P.: 159–161° C.; NMR, MS and IR comply with the structure.

EXAMPLE 46

Preparation of 2,2-dimethyl-propanoic acid 3,4-dihydro-3-(4-methoxy phenyl)-4-oxo-2H-1-benzopyran-7-yl ester

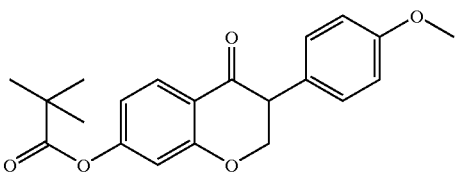

Compound of Ex 45 dissolved in dioxane and hydrogenated in a Parr apparatus at 35 psi with Pd/$BaSO_4$ 5% as catalyst.

After 3 hours the catalyst was filtered off, the solution was evaporated to a little volume and quenched into water to obtain a precipitate that was filtered and dissolved in hot 95% ethanol. After standing overnight in a refrigerator, the white product was filtered and washed with petroleum ether, to obtain 66 g of the title compound.

M.P.: 119–121° C.; NMR, MS and IR comply with the structure.

EXAMPLE 47

Preparation of 2,2-dimethyl-propanoic acid 3,4-dihydro-4-hydroxy-3-(4-methoxyphenyl)-4-[[4-(phenylmethoxy)phenyl]methyl]-2H-1-benzopyran-7-yl ester

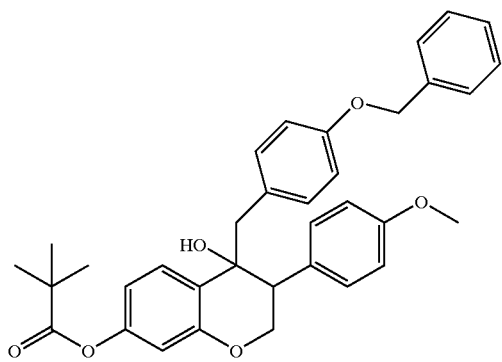

Mg turnings (15.4 g, 635 mmol) were loaded into a 2 liter flask; 4-benzyloxybenzyl chloride (49.6 g, 211.6 mmol) was dissolved in dry THF and this solution was dropped in one hour on the Mg turnings under an inert atmosphere while maintaining a gentle reflux.

The mixture was refrigerated to −20° C., then a solution of compound of ex. 46 (60 g, 169.3 mmol) in dry THF (300 ml) was dropped in a 15 minutes period. After leaving the mixture to reach r.t., water (50 ml) was added, the solid material was filtered off and the solution was evaporated to dryness. Ethyl acetate (200 ml) was added to the residue oil and the mixture was allowed to stay at −20° C. for one hour. The solid was filtered off and the solution was evaporated to dryness. The residue oil was crystallised from a 80/20 mixture of 95% ethanol and petroleum ether to give 60.8 g (110 mmol) of the title compound.

M.P.: 104–111° C.; NMR, MS and IR comply with the structure.

EXAMPLE 48

Preparation of 2,2-dimethyl-propanoic acid 3,4-dihydro-4-hydroxy-4-[(4-hydroxyphenyl)methyl]-3-(4-methoxyphenyl)-2H-1-benzopyran-7-yl ester

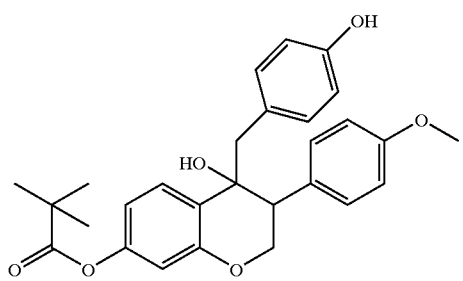

Compound of ex. 47 (60.8 g, 110 mmol) was dissolved in ethyl acetate, 5% Pd/C was added and the mixture was hydrogenated.

The catalyst was filtered off and the solution was evaporated to dryness obtaining a solid foam (50.88 g, 110 mmol) that was used without any further purification.

NMR, MS and IR comply with the structure.

EXAMPLE 49

Preparation of 2,2-dimethyl-propanoic acid 3,4-dihydro-4-hydroxy-3-(4-methoxyphenyl)-4-[[4-[2-(1-piperidinyl)ethoxyl]phenyl]methyl]-2H-1-benzopyran-7-yl este

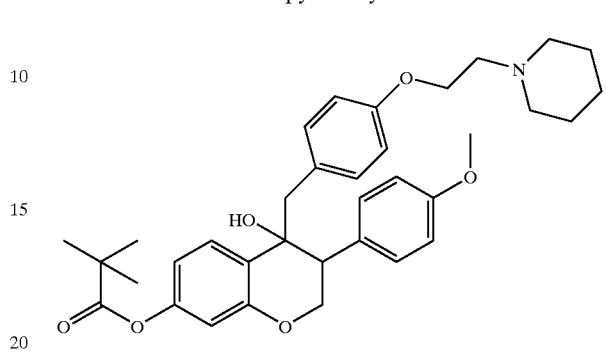

A mixture of: compound of ex. 48 (50 g, 108.1 mmol), N-(2-chloroethyl)piperidine hydrochloride (20 g, 108.7 mmol) and K$_2$CO$_3$ in boiling acetone (860 ml) was allowed to react.

The solid was filtered off and the solution was evaporated to dryness obtaining an oil (62 g, 108.1 mmol) that was used without any further purification.

NMR, MS and IR comply with the structure.

EXAMPLE 50

Preparation of 3,4-dihydro-4-hydroxy-3-(4-methoxyphenyl)-4-[[4-[2-(1-piperidinyl)ethoxyl]phenyl]methyl]-2H-1-benzopyran-4,7-diol

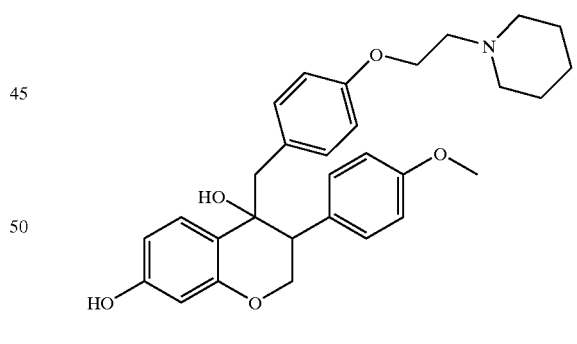

To a solution of compound of ex. 49 (60 g, 104.6 mmol) in methanol, K$_2$CO$_3$ dissolved in water was added and allowed to react at r.t. for 3 hours. The solvent was evaporated to 300 ml and the mixture was quenched into water and stirred overnight. The solid was filtered, washed with water and dried under vacuum at r.t. obtaining 36 g of crude product that was crystallised from boiling acetonitrile to; obtain 28 g of the compound.

M.P.: 107.5–108.5° C.; NMR, MS and IR comply with the structure.

EXAMPLE 51

Preparation of 3-(4-methoxy)phenyl-4-[[4-[2-(1-piperidinyl)ethoxyl]phenyl]methyl]-2H-1-benzopyran-7-ol hydrochloride

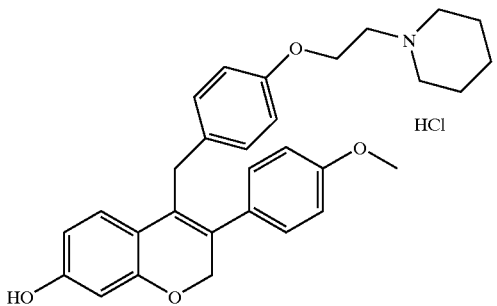

Compound of ex. 50 (24 g, 49 mmol) was dissolved in hot acetonitrile (550 ml), 37% HCl (4.9 ml) was added and the solution was stirred at reflux for 45 minutes. The mixture was allowed to reach r.t. and the crystallised solid was filtered and washed with diethyl ether. 17.3 g (34 mmol) of the title compound were obtained.

M.P.: 199–205° C. (dec.); NMR, MS and IR comply with the structure.

The compounds of the invention have been tested for their pharmacological activity.

In the following examples the results obtained with the compounds 3-phenyl-4-(4-(2-(N-piperidinyl)ethoxy)benzyl)-7-hydroxychrom-3-ene (the compound of example 39 employed as a free base or methansulphonic salt) and 3-(4-methoxy)phenyl-4-[[4-[2-(1-piperidinyl)ethoxyl]phenyl]methyl]-2H-1-benzopyran-7-ol hydrochloride (the compound of example 51), cited in the following as Compound I (example 39) and Compound II (example 51) are reported.

In Vitro Study—Human Estrogen Receptor-α and -β (ER-α and ER-β)

The experiment has been conducted as described in Obourn J D et al, Biochemistry 32, 6229, 1993.

The Compound I of the invention binds with high affinity to the human ER-α and ER-β Binding $K_i$ were 0.041±0.011 and 0.157±0.028 nM, respectively.

Compared with the well-known SERM raloxifene, its ER-α affinity was similar ($K_i$=0.071±0.008 nM), whereas the affinity for ER-β was 10 fold higher ($K_i$=1.62±0.348 nM).

The Compound II of the invention binds with even higher affinity to the human estrogen receptor ER-α and ER-β. Binding $K_i$ were 0.017±0.002 and 0.099±0.005 nM, respectively.

Compared with the well known SERM raloxifene ($K_i$ ER-β=1.62±0.348, ER-α=0.071±0.008 nM), the affinity for ERβ was 16 fold higher, is whereas the affinity for ER-α was similar.

In Vivo Studies—Immature Female Rat Assay.

Antiuterotrophic Activity

Experiments have been conducted as described in Eppenberger U et al, Am J Clin Oncol 14 (suppl. 2), S5–S14, 1991.

In immature female rats, treatment with 17α-ethynil estradiol (E2) at 0.05 mg/kg per os for 3 days significantly increased uterine wet weight (170–220%) compared with vehicle-treated controls.

This concentration of E2 was the lowest producing near-maximal effect and was chosen on the basis of preliminary dose-response experiments.

The Compounds I and II administered orally inhibited the uterotrophic action of E2 in a dose related fashion. Total antagonism was observed with Compound I at 1–10 mg/kg/day ($EC_{50}$=0.33 mg/kg·day), whereas the reference compound levormeloxifene only partially antagonized E2 stimulation of the uterus (40–45% inhibition at 1 mg/kg/day).

Total antagonism was observed with Compound II at 0.1–1 mg/kg·day. Comparison of the antioestrogenic potencies (ED50=dose required to produce 50% reduction in estradiol-stimulated growth) showed that the Compound II of the invention was about 25 times more potent than raloxifene (ED50=0.016 and 0.39 mg/kg·day, respectively).

Uterotrophic Activity

The Compound I and raloxifene at 0.1 mg/kg/day slightly increased uterine weight compared with vehicle treated control rats (17 and 32%, respectively, significantly less than 0.1 mg/kg/day E2); however, uterine weight for 0.01, 1 and 10 mg/kg/day of the Compound I and raloxifene were not significantly different from control rats.

Uterine weights for 0.01, 0.1, 1 and 10 mg/kg·day of the Compound II and raloxifene were not significantly different from control rats.

In line with previously reported data (M. Salman et al., J. Med. Chem. 1986, 29, 1801–1803), levormeloxifene at the same dose levels significantly increased uterine wet weight in a dose-depend way and a maximal agonist activity of 60–65% that of E2 was apparent at 1 mg/kg.

We can conclude that in the immature female rat assay, the preferred compounds of the invention appeared potent and effective in antagonizing estrogen stimulation of the uterus down to the level of vehicle treated controls with no significant estrogenicity.

The Compound II appeared more potent than raloxifene in antagonizing estrogen stimulation of the uterus.

In contrast, levormeloxifene was a partial agonist, demonstrating at 1 mg/kg-day a maximal agonist activity of 60–65% that of E2.

The pharmacological profile of the claimed compounds in immature rats appears strictly different compared with the one of the structurally related compound levormeloxifene, indicating that the structural differences between the compounds of the invention and those of the prior art are relevant in reducing the uterine-stimulating effects.

Effects in the Ovariectomized (OVX) Rat Model

The experiments have been conducted according to Kaln D N, Bone Mineral 15, 175–192, 1991 and Grese T A et al J Med Chem 40, 146–167, 1997.

Four-week OVX Rat Assay

The effects of the tested compounds were evaluated also in 9–11-month-old OVX rats that were dosed for 4 weeks post-surgery and compared with OVX and Sham controls.

Tissue-specific estrogen agonist effects were examined utilizing uterine weight, uterine histology, uterine eosinophil peroxidase activity (EPO), bone mineral density (BMD), and serum cholesterol levels as end points.

The administration for 4 weeks was not associated with any overt signs of toxicity.

Effect on Bone Mineral Density (BMD) (Lumbar Spine L1-4)

Bone mineral density (BMD) was measured by DEXA (Dual Energy XRay Absorptiometry) using a Hologic QDR- 1000 plus instrument equipped with dedicated software for small animal measurements. An ultrahigh-resolution mode (line spacing 0.0254 cm and resolution 0.0127 cm) was used with a collimator of 0.63 mm diameter. This technique provides an integrated measure of both cortical and trabecular bone.

In vivo DEXA measurements were carried out immediately before surgery (baseline scan) and 4 weeks after surgery. The anatomic region examined was the lumbar spine L1-4.

All animals were anesthetized before scanning with a mixture of ketamine and p-promazine. For each scan a rat was placed in a supine position with the spine parallel to the long axis of the densitometer table. The lumbar spine was scanned using the pelvic bones as landmark; analysis of this site was accomplished by dividing vertebra and intervertebral spaces with subregional high resolution software and including only target vertebra in the global region of interest.

Percent protection was calculated by the following formula: % protection=[(% chance $BMD_{test\ compound}$-% chance $BMD_{OVX\ control}$)/(% chance $BMD_{sham\ control}$-% chance $BMD_{OVX\ control}$)]×100.

In a first experiment the bone sparing effects of Compound I were determined.

4 weeks after surgery a significantly lower percent change in BMD from baseline in OVX rats compared to sham rats was observed (−9.39±0.60 and −0.11±0.75%, respectively $P<0.01$).

As shown in the literature, 0.1 mg/kg of 17α-ethynil estradiol (E2) partially prevented the loss of bone (~50% protection).

0.1-, 1 and 10 mg/kg/day of the Compound I treatment reduced the bone loss, as their % change in BMD from the baseline was significantly higher compared to OVX rats (40,46 and 47% protection, respectively, $P<0.01$).

In a second experiment the bone sparing effects of Compound II were determined.

4 weeks after surgery a significantly higher bone loss from baseline in OVX rats compared to sham rats was observed (% change in BMD −5.16% and +1.28%, respectively $P<0.01$).

As shown in the literature, 0.1 mg/kg of 17α-ethynil estradiol (E2) prevented the loss of bone (~95% protection).

0.1 and 1 mg/kg·day of the tested compound treatment reduced the bone loss in a dose dependent manner, as their % change in BMD from the baseline was significantly higher compared to OVX rats (60 and 119% protection, respectively, $P<0.01$).

The bone sparing effects of the tested compounds was comparable with those achieved with E2 0.1 mg/kg·day, indicating that they are full oestrogen agonists on bone.

Raloxifene and levormeloxifene were compared to Compoud II: their protective effect was significant (50–60% protection at 1 and 10 mg/kg·day) but significantly lower compared to the compound of the invention.

Effect on Serum Cholesterol Levels 0.1–10 mg/kg day of the Compound I dose-dependently decreased total serum cholesterol in OVX rats with half maximal efficacy $ED_{50}$ of 0.12 mg/kg and maximal lowering of cholesterol observed at 10 mg/kg. (67% inhibition relative to the OVX control).

0.1 and 1 mg/kg·day of the Compound II dose-dependently decreased total serum cholesterol in OVX rats (75 and 81% inhibition respectively). Compound II was as efficacious as E2 in lowering serum cholesterol levels with respect to controls, whereas raloxifene and levormeloxifene appeared significantly less potent.

Uterine Effects

In OVX rats treated with the compounds of the invention at 0.1, 1 and 10 mg/kg·day, uterine weight was significantly lower than both sham controls and E2-treated OVX rats.

The degree of eosinophilic peroxidase induction of the uterus may be a useful marker for estrogen-effected growth responses (Lyttle C R and DeSombre E R Proc Natl Acad Sci USA 74, 3162–3166, 1977). The tested compounds had no significant effect on eosinophilic peroxidase activity compared to OVX uteri, whereas levormeloxifene significantly increased this parameter.

Moreover, the tested compounds administration was not associated with significant stimulation of uterine epithelia.

Instead, estrogen and levormeloxifene that caused full disappearance of epithelium atrophy, maintained endometrium histology at the levels of sham controls.

Compound I and II of the invention respectively administered at 0.1, 1 and 10 mg/kg/day and 0.1 and 1 mg/kg/day for 4 weeks by oral route, significantly reduced bone loss while lowering serum cholesterol levels.

These protective effects were achieved at a dose with minimal uterine stimulation.

Taken together, the reported results show that the benzopyran derivatives of the invention are provided with an interesting SERM (Selective Estrogen Receptor Modulation) activity, comparing favorably in tissue selectivity with the structurally related reference compounds of the prior art.

In Vitro Study—MCF-7 Cell Proliferation

In this test the Compound I has been compared with the two marketed products, raloxifene and tamoxifene.

The tumor cells were obtained from American Type Culture Collection (ATCC HTB-22). The culture media used was Minimum Essential medium with 10% fetal bovine serum, and media were supplemented with 1% antibiotic-antimycotic. Aliquots of 100 μl of cell suspension (5×103/well) were placed in 96-well microtiter plates in an atmosphere of 5% $CO_2$ at 37° C. After 24 hours, 100 μl of growth medium, 2 μl of test solution, mitomycin or vehicle (DMSO, final concentration 0.4%), was added respectively per well in duplicate for an additional 72-hours incubation. At the end of incubation, 20 μl of alamarBlue 75% reagent was added to each well for another 6-hour incubation before detection of cell viability by fluorescent intensity (excitation at 530 nm and emission at 590 nm).

The Compound I and two comparison compounds, raloxifene and tamoxifene exhibited significant growth inhibition relative to the vehicle treated control group at concentrations between 1 and 100 μM. Further, under the conditions of this experiment, tamoxifene and the Compound I were more potent (Inhibitory Concentration $IC_{50}$= 6.0 and 6.5 μM, respectively) than raloxifene ($IC_{50}$=11 μM).

Total growth inhibition was observed at 11 μM for tamoxifene and the Compound I or 18 μM for raloxifene, whereas the 50% lethal concentrations (LC50) were 22 (tamoxifene), 20 (Compound I) and 29 (raloxifene) μM.

The reported results confirm that the compounds of the invention act as a potent and selective tissue-specific estrogen agonist and antagonist.

The tested compounds have a better pharmacological profile than the structurally related reference compound benzopyran derivative levormeloxifene and compare favourably with raloxifene, one of the first SERMs developed for clinical use.

In view of their therapeutic use, the compounds of the invention can be opportunely combined with the usual pharmaceutically acceptable excipients for the preparation of pharmaceutical compositions for parenteral, oral, nasal, rectal, subdermal or transdermal administration according to conventional methods.

One skilled in this art may formulate the compounds in an appropriate manner, and in accordance with accepted practices, such as those disclosed in *Remington's Pharmaceutical Sciences*, Gennaro ed., Mack Publishing Co., Easton, Pa. 1990.

What is claimed is:

1. A 2H-1-benzopyran of general formula:

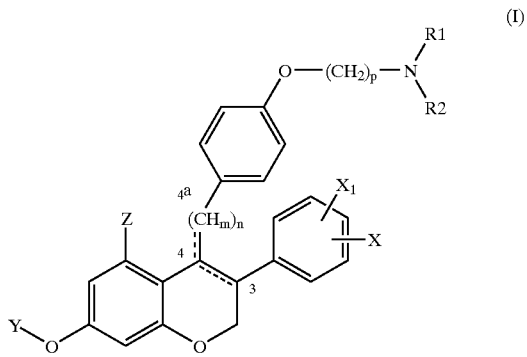

wherein $R_1$ and $R_2$ are independently H, alkyl, haloalkyl, alkenyl or haloalkenyl, or, when they are alkyl, together with the nitrogen atom they are bound to, they can form a 4- to 8-membered heterocyclic ring;

X is H, alkyl, aryl, nitro, halo, or O—$R_3$ wherein $R_3$ is H, alkyl, aryl, alkanoyl, or aryloyl;

$X_1$ is H, alkyl or alkoxy and when X and $X_1$ are alkyl they can form, together with the carbon atoms they are bound to, a fused aromatic ring to give an α-naphthalenyl;

Y is H, alkyl, alkanoyl, aryloyl, alkylaminocarbonyl, or alkyloxycarbonyl;

Z is H, or O—$R_4$ wherein $R_4$ is H, alkyl, alkanoyl, or aryloyl;

m is 1, 2;

n is 0, 1;

p is 2–6; and

====represents a single or double bond between the atoms in positions 3-4 or 4-4a;

when n is 1 the double-bond may be alternatively exocyclic or endocyclic to give respectively a 4-benzylidenechroman for m=1 or a 4-benzyl-chrom-3-ene for m=2;

when n is 0, represents a single or double band between the atomi in position 3-4, and represents a single or double bond between the atoms in positions 3-4, and Z is not H;

or a pharmaceutically acceptable salts thereof.

2. The 2H-1-benzopyran of claim 1 wherein:

$R_1$ and $R_2$ are alkyl and together with the nitrogen atom to which they are bound form a piperidine ring, X is H or $C_1$–$C_4$ alkoxy, $X_1$ is H, Y is H, $C_1$–$C_5$ alkanoyl or aryloyl Z is H, m is 2, n is 1, p is 2, the bond between the atoms in position 3-4 is a double bond and the bond between the atoms in position 4-4a is a single bond.

3. The 2H-1-benzopyran of claim 1 which is 3-phenyl-4-(4-(2-(N-piperidinyl)ethoxy)benzyl)-7-hydroxychrom-3-ene, or a salt thereof.

4. The 2H-1-benzopyran of claim 1 which is 3-(4-methoxy)phenyl-4-2H-1-benzopyran-7-ol, or a salt thereof.

5. A pharmaceutical composition comprising:
at least one 2H-1-benzopyran of claim 1, and
at least one pharmaceutically acceptable excipient.

6. A method of treating a postmenopausal pathology comprising:
administering to a patient in need thereof an effective amount of the 2H-1-benzopyran of claim 1 wherein the postmenopausal pathology is at least one pathology selected from the group consisting of osteoporosis, coronary heart disease and estrogen-dependent cancer.

7. A pharmaceutical composition comprising:
at least one 2H-1-benzopyran according to claim 2, and
at least one pharmaceutically acceptable excipient.

8. A pharmaceutical composition comprising:
at least one 2H-1-benzopyran according to claim 3, and at least one pharmaceutically acceptable excipient.

9. A pharmaceutical composition comprising:
at least one 2H-1-benzopyran according to claim 4, and
at least one pharmaceutically acceptable excipient.

10. A method of treating a postmenopausal pathology comprising:
administering to a patient in need thereof an effective amount of the 2H-1-benzopyran of claim 2 wherein the postmenopausal pathology is at least one pathology selected from the group consisting of osteoporosis, coronary heart disease and estrogen-dependent cancer.

11. A method of treating a postmenopausal pathology comprising:
administering to a patient in need thereof an effective amount of the 2H-1-benzopyran of claim 3 wherein the postmenopausal pathology is at least one pathology selected from the group consisting of osteoporosis, coronary heart disease and estrogen-dependent cancer.

12. A method of treating a postmenopausal pathology comprising:
administering to a patient in need thereof an effective amount of the 2H-1-benzopyran of claim 4 wherein the postmenopausal pathology is at least one pathology selected from the group consisting of osteoporosis, coronary heart disease and estrogen-dependent cancer.

13. The 2H-1-benzopyran of claim 1, wherein $R_1$ and $R_2$ together with a nitrogen atom they are bound to form a piperidino ring.

14. The 2H-1-benzopyran of claim 1, wherein $R_1$ and $R_2$ together with a nitrogen atom they are bound to form a pyrrolidino ring.

15. The 2H-1-benzopyran of claim 1, wherein Y is H.

16. The 2H-1-benzopyran of claim 1, wherein Y is alkanoyl.

17. The 2H-1-benzopyran of claim 1, wherein Z is hydrogen and n is 1.

18. The 2H-1-benzopyran of claim 1, wherein Z is hydroxy or alkoxy.

19. The 2H-1-benzopyran of claim 1, wherein n is 1.

20. The 2H-1-benzopyran of claim 1, wherein p is 2.

21. The 2H-1-benzopyran of claim 1, wherein X and $X_1$ are hydrogen.

22. The 2H-1-benzopyran of claim 1, wherein one of X or $X_1$ is hydrogen and the other is halogen or an —$OR_3$ group, wherein $R_3$ is H, alkyl, aryl, alkanoyl, or aryloyl.

23. A method for increasing bone mineral density (BMD) comprising administering to a subject in need thereof an amount of the 2H-1-benzopyran of claim 1 effective to increase bone mineral density.

24. A method for antagonizing estrogen stimulation of the uterus comprising administering to a subject in need thereof an amount of the 2H-1-benzopyran of claim 1 effective to reduce estrogen stimulation of the uterus.

25. A method for reducing serum cholesterol comprising administering to a subject in need thereof an amount of the 2H-1-benzopyran of claim 1 effective to reduce serum cholesterol.

26. A method for reducing the growth of estrogen-dependent tumor cells comprising contacting said cells with an amount of the 2H-1-benzopyran of claim 1 effective to reduce the growth of estrogen-dependent tumor cells.

27. The method according to claim 12, wherein the postmenopausal pathology is at least one pathology selected from the group consisting of osteoporosis, coronary heart disease and estrogen-dependent human cancer.

* * * * *

UNITED STATES PATENT AND TRADEMARK OFFICE
CERTIFICATE OF CORRECTION

PATENT NO. : 6,951,883 B2
DATED : October 4, 2005
INVENTOR(S) : Maurizio Delcanale et al.

It is certified that error appears in the above-identified patent and that said Letters Patent is hereby corrected as shown below:

Column 43,
Lines 57-60, "...when n is O, represents a single or double bond between the atomi in position 3-4, and represents a single or double bond between the atoms in positions 3-4, and Z is not H;" should read
-- when n is O ----- represents a single or double bond between the atoms in positions 3-4, and Z is not H; --.

Signed and Sealed this

Seventh Day of February, 2006

JON W. DUDAS
*Director of the United States Patent and Trademark Office*